US010550691B2

United States Patent
Benoit et al.

(10) Patent No.: US 10,550,691 B2
(45) Date of Patent: Feb. 4, 2020

(54) WORKFLOW FOR EVALUATING STABILIZATION PRODUCTS FOR USE IN SUBTERRANEAN FORMATIONS

(71) Applicant: Halliburton Energy Services, Inc., Houston, TX (US)

(72) Inventors: Denise Nicole Benoit, Houston, TX (US); Antonio Recio, III, Humble, TX (US); Kurt William Hoeman, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 138 days.

(21) Appl. No.: 15/475,595

(22) Filed: Mar. 31, 2017

(65) Prior Publication Data

US 2018/0202289 A1    Jul. 19, 2018

Related U.S. Application Data

(60) Provisional application No. 62/445,844, filed on Jan. 13, 2017.

(51) Int. Cl.
*E21B 49/02* (2006.01)
*E21B 41/00* (2006.01)
(Continued)

(52) U.S. Cl.
CPC ............. *E21B 49/02* (2013.01); *E21B 41/00* (2013.01); *G01N 33/24* (2013.01); *E21B 21/00* (2013.01);
(Continued)

(58) Field of Classification Search
None
See application file for complete search history.

(56) References Cited

U.S. PATENT DOCUMENTS

2016/0131628 A1    5/2016  Fontenelle et al.

FOREIGN PATENT DOCUMENTS

WO    2016/072989 A1    5/2016

OTHER PUBLICATIONS

Conway et al. "An Examnation of Clay Stabilization and Flow Stability in Various North American Gas Shales", SPE 147266 Oct. 2011, 17 pages.*

(Continued)

*Primary Examiner* — Angela M DiTrani Leff
*Assistant Examiner* — Charles R Nold
(74) *Attorney, Agent, or Firm* — Thomas Rooney; Baker Botts L.L.P.

(57) ABSTRACT

Methods of evaluating formation stabilization treatments for subterranean formations are provided. In some embodiments, the methods comprise: providing; adding a portion of test fluid to each of a first and second portion of a material from a subterranean formation and agitating to form a first mixture and a second mixture; measuring capillary suction time of the first mixture and turbidity of the second mixture; placing a sandpack comprising another portion of the formation material in a column; passing another portion of the test fluid through the sandpack to collect an effluent; measuring a differential pressure across the sandpack and a turbidity of the effluent; and selecting a formation stabilization treatment for the subterranean formation based at least in part on one or more of the capillary suction time of the first mixture, the turbidity of the second mixture, the differential pressure across the sandpack, and the turbidity of the effluent.

15 Claims, 15 Drawing Sheets

(51) Int. Cl.
   *E21B 43/26* (2006.01)
   *E21B 43/25* (2006.01)
   *G01N 33/24* (2006.01)
   *E21B 37/00* (2006.01)
   *E21B 21/00* (2006.01)
   *G01N 33/28* (2006.01)

(52) U.S. Cl.
   CPC ............... *E21B 37/00* (2013.01); *E21B 43/25* (2013.01); *E21B 43/26* (2013.01); *G01N 33/2823* (2013.01); *G01N 33/2835* (2013.01)

(56) References Cited

OTHER PUBLICATIONS

"RockPerm™ Service" Halliburton Energy Services, Inc. Jun. 2015 (3 pages).
Program for SPE International Conference on Oilfield Chemistry, Apr. 3-5, 2017 (36 pages).
Zhang, Junjing, Ding Zhu, and A. Daniel Hill. "Water-induced damage to propped-fracture conductivity in shale formations." SPE Production & Operations 31, No. 02 (2016): 147-156. (10 pages).
Zhang, Junjing. "Fracture conductivity damage by water in shale formations." Proceedings of the SPE Annual Technical Conference and Exhibition, Amsterdam, The Netherlands, Society of Petroleum Engineers, 2014. (14 pages).
Benoit, Denise, Antonio Recio, Ruslan Gashimov, Dandan Hu, Kristina Holan, and Kurt Hoeman. "In-Depth Analysis of How Chemical Treatments Work to Improve Conductivity in Shale Formations." In SPE International Conference on Oilfield Chemistry. Society of Petroleum Engineers, 2017. (13 pages).
Benoit, Denise, et al. "In-Depth Analysis of How Chemical Treatments Work to Improve Conductivity in Shale Formations." Microsoft Powerpoint presentation, Apr. 2017(16 pages).
Recio, Antonio, Denise Benoit, Kristina Henkel, and Kevin York. "Which Cations are Detrimental to Shale Preservation?" In SPE International Conference on Oilfield Chemistry. Society of Petroleum Engineers, 2017. (17 pages).
Recio, Antonio, et al. "Which Cations are Detrimental to Shale Preservation?" Microsoft Powerpoint presentation, Apr. 2017(16 pages).

* cited by examiner

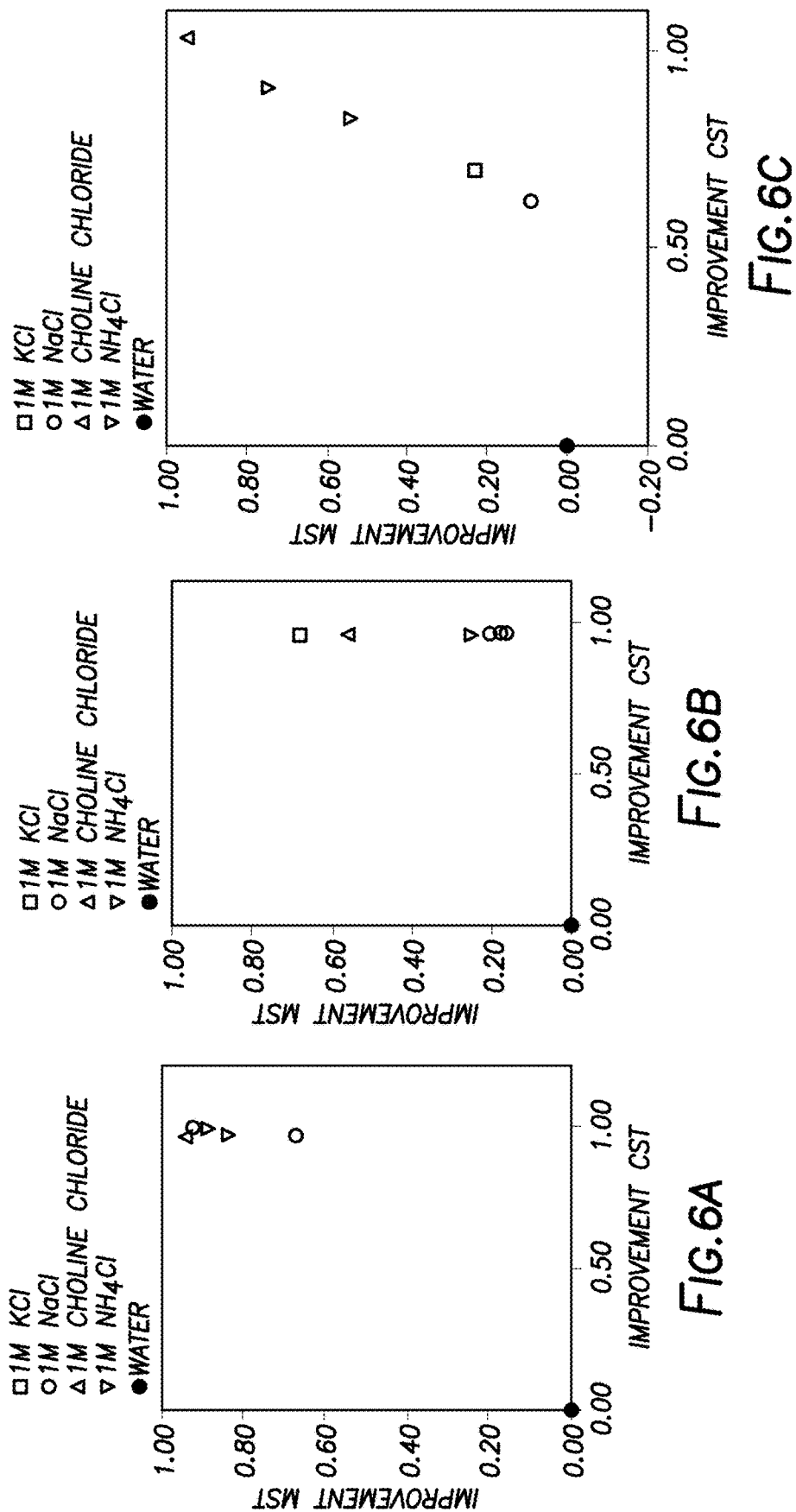

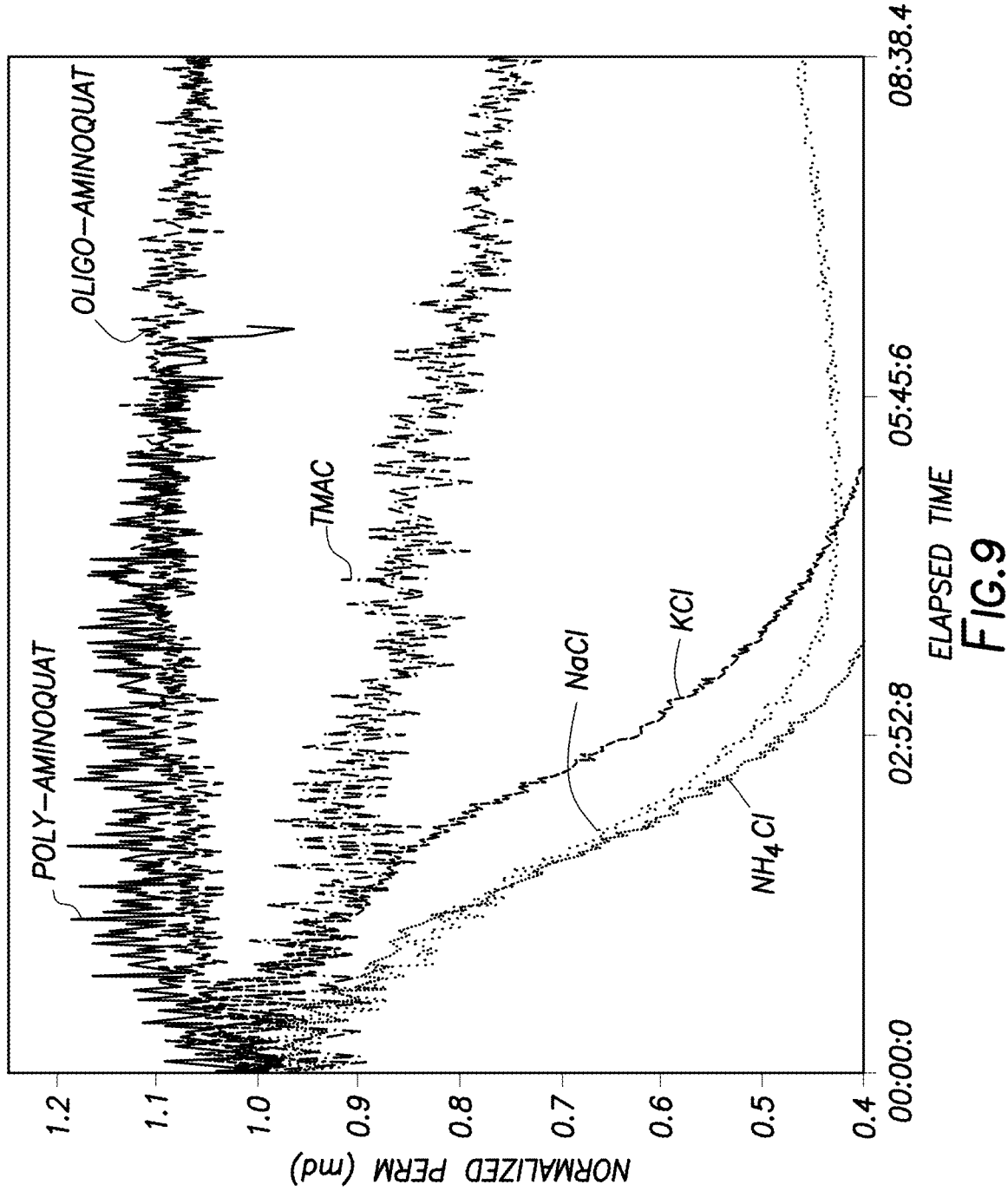

WORKFLOW FOR EVALUATING STABILIZATION PRODUCTS FOR USE IN SUBTERRANEAN FORMATIONS

CROSS-REFERENCE TO RELATED APPLICATIONS

The present application claims priority to U.S. Provisional Application Ser. No. 62/445,844 filed on Jan. 13, 2017, entitled "Improvements to Formation Stabilization Product Recommendation Workflow," the entire disclosure of which is incorporated herein by reference.

BACKGROUND

The present disclosure relates to systems and methods for treating subterranean formations.

Production of oil and gas from subterranean formations may be hindered by formation damage. Most damage occurs due to introduction of fluids and high pump rates that cause swelling and/or migrating in the formation. Formations are prone to water-sensitivity, which can cause damage through swelling, softening, dissolving, forming precipitates, sloughing and/or generating migrating fines. All of these can decrease production or induce wellbore damage.

In some formations, clays or fines may already be present or fines may be generated during formation treating activity. In some instances, the formation is stable causing no obstruction to the flow of hydrocarbons through the subterranean formation. However, when the formation is not stable, the minerals can swell and/or fines can migrate through the formation until they become lodged in pore throats, thereby decreasing the permeability of the formation. Methods for evaluating formation stabilization treatments typically rely on expensive instrumentation, time-consuming methods, and hard to obtain core materials; which are not feasible to run on a well-to well basis at a field lab locale. Moreover, many such methods may not accurately identify the damage mechanisms in a particular formation, and thus may provide insufficient information to identify the effective treatments to reduce that damage.

BRIEF DESCRIPTION OF THE DRAWINGS

These drawings illustrate certain aspects of some of the embodiments of the present disclosure, and should not be used to limit or define the claims.

FIGS. 6A-6C are a series of plots illustrating data regarding cation performance on pure clay and shale materials.

FIG. 9 is a graph illustrating data relating to the performance of different brines and treatments in column flow tests according to certain embodiments of the present disclosure.

Figure 1:
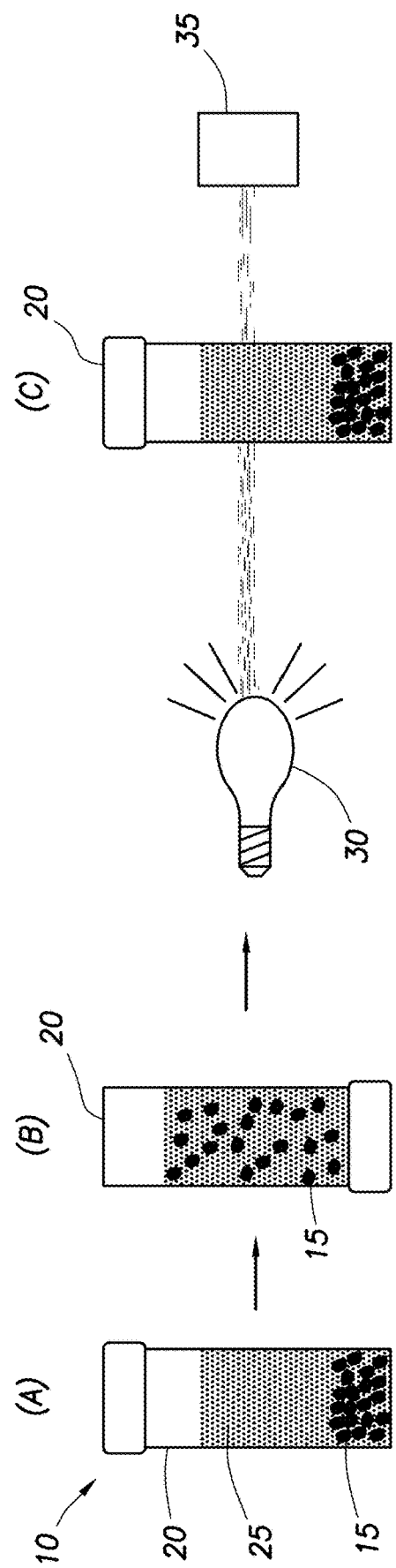
FIG. 1 is a diagram illustrating an example of a formation stability turbidity test.

While embodiments of this disclosure have been depicted, such embodiments do not imply a limitation on the disclosure, and no such limitation should be inferred. The subject matter disclosed is capable of considerable modification, alteration, and equivalents in form and function, as will occur to those skilled in the pertinent art and having the benefit of this disclosure. The depicted and described embodiments of this disclosure are examples only, and not exhaustive of the scope of the disclosure.

DESCRIPTION OF CERTAIN EMBODIMENTS

The present disclosure relates to systems and methods for treating subterranean formations. More particularly, the present disclosure relates to methods of evaluating and/or selecting formation stabilization treatments for subterranean formations.

The methods and systems of the present disclosure implement a workflow of tests that are used to evaluate different formation stabilization treatments for use in a particular subterranean formation. According to certain embodiments of the present disclosure, methods of selecting a formation stabilization treatment product for a subterranean formation comprise: obtaining a formation material from a subterranean formation; adding a first portion of a test fluid to a first portion of the formation material to form a first mixture, the test fluid comprising the formation stabilization treatment product; adding a second portion of the test fluid to a second portion of the formation material to form a second mixture; agitating the first and second mixtures; measuring capillary suction time of the first mixture; measuring turbidity of the second mixture; placing a test sandpack comprising a third portion of the formation material in a column; passing a third portion of the test fluid through the test sandpack to collect an effluent; measuring differential pressure across the test sandpack; measuring turbidity of the effluent; and selecting a formation stabilization treatment for the subterranean formation based at least in part on one or more of the capillary suction time of the first mixture, the turbidity of the second mixture, the differential pressure across the test sandpack, and the turbidity of the effluent.

The swelling stability test (SST) uses slurries containing formation materials at a set size, ratio to fluids, and prepared with consistent shear stress and time to measure the capillary suction time (swelling tendency) of formation materials in the presence of a treatment fluid. A slurry of formation materials and treatment fluid is generated, and the time required for the free liquid to travel a calibrated distance in a standard porous paper is measured. The measurement is made by placing a certain volume of slurry into a sample cylinder that is resting on a standard porous paper. Electrodes located at two different distances from the edge of the cylinder are connected with a timer. The timer starts when liquid reaches the closest electrode and then stops when it reaches the outer electrode. The time interval measured is sensitive to the amount of free water in the slurry and the permeability of the filter cake deposited. The capillary suction time is recorded in seconds, and the final reported value is the value in a SST test of a blank fluid (run without solids) subtracted from the value of the SST test performed with a slurry. As the formation material swells, it takes up free water from the slurry, which decreases available water to wick through the filter paper. Therefore, the lower the capillary suction time, the less the formation materials swell in that treatment fluid.

The SST method can measure the ability for a chemical additive to prevent clay swelling. The SST test measures the swelling tendency of formation materials when exposed to various fluids. However, the test may be sensitive to changes in the sample preparation that include particle size, shear rate, and shear time. To address these sensitivities, a SST method may be used to provide more consistently prepared test slurry samples and allows for comparison of a variety of formation materials based on their fluid induced swelling damage. The SST method may discern differences in formation materials based on composition and can readily differentiate between products and product concentrations for smectite and mixed-layer clay minerals. However, not all fluid induced damage is a result of swelling clays and there is a relatively high abundance of illite and kaolinite clay minerals in North American shale formations. These formations may not provide a significant difference in response when tested with the SST test.

Formation stability may be measured by a Mechanical Stability Turbidity (MST) test, which measures damage to the formation materials caused by a fluid, including but not limited to softening, fines migration and sloughing. The propensity of the sample to disintegrate and release suspended fine materials is determined by measuring the turbidity of the solution. FIG. 1 illustrates a process 10 for an MST in certain embodiments of the present disclosure, which entails at step (A) the placement of formation cuttings 15 into a vial 20 containing a treatment fluid 25 and then rotating the vial during step (B) to impart mechanical agitation. This procedure exposes the formation cuttings 15 to a number of forces, including but not limited to particle-to-particle collisions, particle-to-wall shear forces, particle-to-wall impact forces, and/or particle-to-fluid drag forces. In step (C), turbidity measurements are then obtained to quantify the fine materials suspended in a fluid at various time points in the process, as a function of the amount of light from a light source 30 that passes through the vial 20 to a detector 35 on the opposite side of the vial. Higher turbidities indicate more fluid induced destabilization of the formation materials. In the end, a treatment product that generates lower turbidity is indicative of an effective formation stabilization treatment.

During the MST test, separation of damage and undamaged samples occurs and the settling rate in the fluid is used, which is proportional to particle size of the particles and their density difference of the fluid. Initial particle size of the materials used in testing may be chosen to help ensure that the undamaged materials will settle out of the sample, leaving only the generated fines suspended in solution for each reading. In some embodiments, the instrument may take an average of 6.0 seconds to take a measurement and, within that time, only material of ~5 microns or less may be captured in the reading (~1.3% of the starting size and much larger than a single clay platelet). A potential source of error in some sample flocculation or precipitation of the test materials causes the fines to behave as larger particles and not suspend, which can lead to compromised turbidity measurements. However, the results obtained with the MST may have less than 5% variability and correlate well with the Brinell hardness of materials.

Running SST and MST in combination gives a comparison of the fluid damage/protection potential based on multiple damage mechanisms. Changes in the SST correlate most closely with the composition of swelling clay minerals tendency while the MST reflects changes in the rock hardness and mechanical integrity. Both methods are easy to run, bench-top tests that require little time, material or cost to evaluate formation materials in most relevant fluids. Treatment fluids can be doped with varying amounts of mineral protective chemical additives to determine optimal treatments and treatment concentration. Moreover, the testing methods can be used to evaluate the damage potential of formation materials in the fluids designed for the stimulation treatment.

In the methods and systems of the present disclosure, a column flow (CF) test may be used to evaluate damage in the formation material when it comes into contact with water by measuring (a) the differential pressure across a column containing a sandpack comprising formation material, and (b) the turbidity of effluent collected from a fluid passed through the sandpack comprising formation material. The CF tests in the methods and systems of the present disclosure may utilize any apparatus suitable for performing such tests. In some embodiments, an apparatus for a CF experiment may be prepared by first preparing a sandpack that comprises materials from the formation. For example, premium white sand may be combined with formation materials that have been sieved to the same particle size as the sand grains and then gently mixed until homogeneous. A small screen may be placed at the bottom of the column and the mixture of sand and cuttings is gravity packed on the screen. The column then may be compacted using gentle agitation. Once the top of the sandpack reaches an equilibrium, a second screen may be placed on top of the sandpack to hold it in place. Next, the treatment fluid to be applied to the sandpack may be prepared and placed in a reservoir that is fixed in communication with the column with the sandpack. Additional fluid reservoirs may be filled with fresh or deionized (DI) water fixed in communication with the column with the sandpack. This volume of water will be used to "challenge" the treatment applied to the sandpack.

Figure 2:
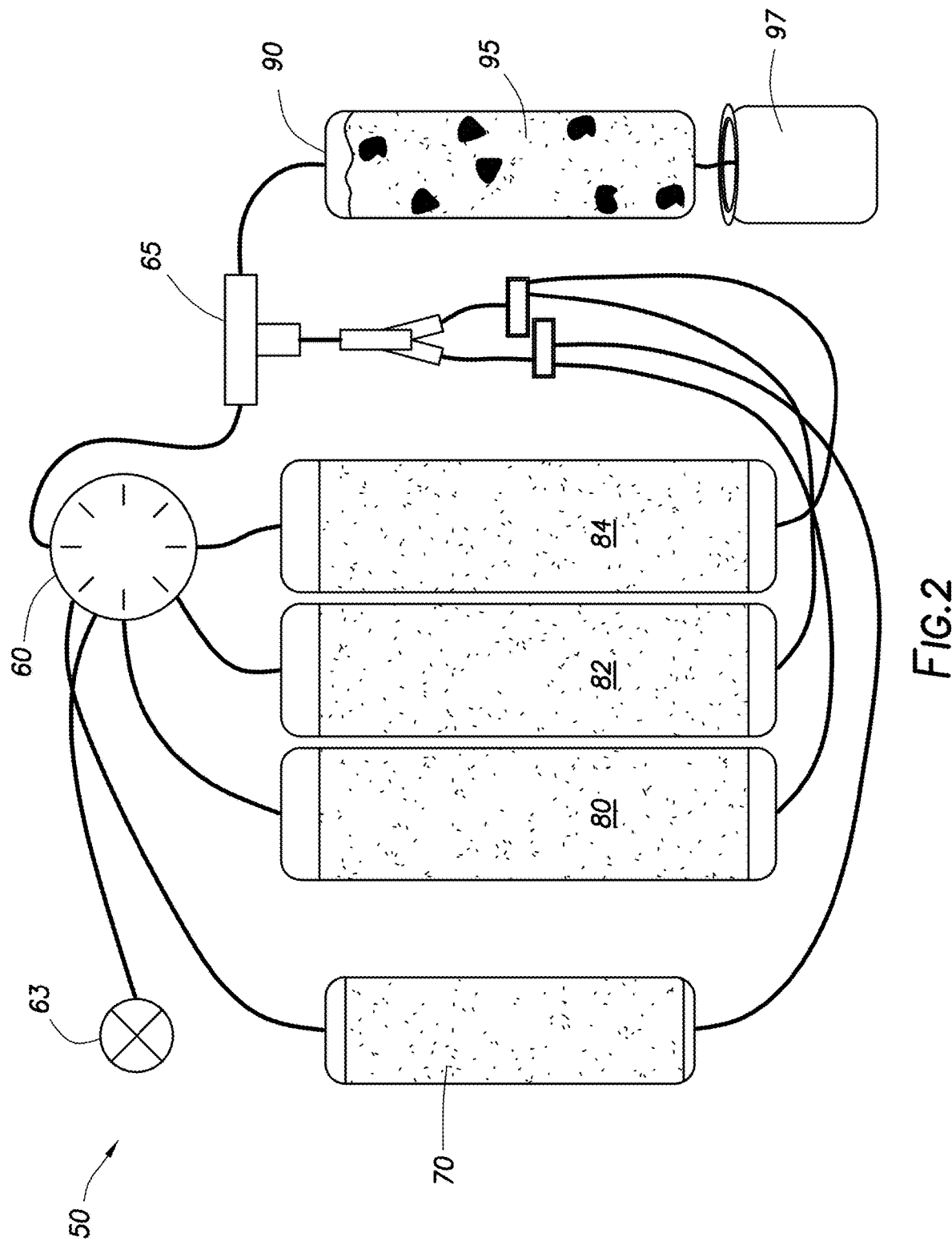
FIG. 2 is a diagram illustrating an example of a system for a column flow test.

An example of an automated system 50 that may be used to perform CF tests in certain embodiments of the present disclosure is shown in FIG. 2. As shown, the system 50 is fitted with a number of components that are representative of a miniature core flow system. The CF system 50 makes use of an airflow regulator 60 that contains a pressure transducer 63. Air then flows from a multivalve port 65 capable of selecting which fluid reservoir or sandpack to energize based on the type of experiment performed. Treatment fluid from reservoir 70 or water from reservoirs 80, 82, and/or 84 may be pumped into column 90 where they pass through prepared sandpack 95. Fluids that are eluted from the sandpack 95 and column 90 may be captured in a vial 97 allowing for additional analysis of the "produced" fluid.

In some embodiments, the CF test may be performed in three stages. In the first stage in the CF process, the gas permeability of each sandpack before introducing any fluid may be measured. This may be done by passing nitrogen gas through the sandpack column and measuring the pressure difference across the sample. This step gives the initial permeability of the pack before any fluid contact and an analysis for the pack-to-pack consistency for the test. In the second stage, treatment fluids (or water) are pumped from the fluid reservoir into the sandpack. As the fluid is exposed to the formation materials, a pressure differential is created and recorded and evaluated for damage during treatment. The fluid that eluted from the sandpack column may be collected and sampled for turbidity. In the third stage or the "challenge" phase, fresh DI water from the fluid reservoirs may be pumped through the sandpack column at different flowrates and the differential pressure may be recorded. The flow rates are generally selected to be sufficiently high to cause sufficient mechanical damage to the formation material that is observable in the differential pressure and significantly varies with changes in the flow rate. The fresh water that eluted from the sandpack column also may be collected for further analysis.

The data from the CF test may provide information relating to various aspects of fluid- and flow-induced damage in the formation materials. For example, a higher pressure differential may indicate the presence of swelling or mechanical damage (e.g., plugging) of the formation that is generally not due to fines production (unless the amount of fines generated is so large that it plugs the pore spaces in the formation). In some embodiments, the amount of fines produced in the eluted fluid may be observed as a function of time and flow rate. For example, if the amount of fines in the eluted fluid increases with increasing flow rate, then fines production is likely the primary damage mechanism in the formation. The monitoring of pressure differential and turbidity from the CF test over time during the third stage also may provide information relevant to determining (a) the concentration of a treatment (i.e., how much treatment product per formation surface area is required for a particular treatment fluid to be in contact with the formation) before it effectively reduces damage, (b) the latency of a treatment (i.e., the amount of time that a particular treatment should be in contact with the formation to treat the formation) and/or (c) the permanency of a treatment after the treatment fluid is no longer present. This concentration, latency, and/or permanency information may be used in selecting and/or tailoring stabilizing treatments for a formation as well as determining their frequency.

According to certain embodiments of the present disclosure, methods of selecting a formation stabilization treatment include the following stages. The first stage evaluates the formation material's sensitivity to water by monitoring the prevalence of: (a) swelling using a SST test, (b) formation stability using a MST test, and (c) fines production using a column flow (CF) test. These initial tests determine the amount of fluid damage that is possible for a given formation and determines the next set of steps. According to certain embodiments, standard water analysis and/or formation X-ray diffraction analysis optionally may be performed to obtain additional information.

If the formation shows sensitivity to water in the first stage (e.g., the results of the SST test, MST test, and/or CF test exceed a predetermined threshold), the method moves to the second stage in which possible treatments or treatment products are evaluated for a given formation. The top performing product may be determined based on percent improvement of SST, MST, and/or CF with the product. In some embodiments, the SST and/or MST tests may be run with the possible treatments before the CF tests, among other reasons, to select a subset (i.e., one or more) of the possible treatments for evaluation with the CF test. The CF test then may be used on that subset of products to select a single treatment or treatment product from among them or confirm that the treatment selected based on the SST and/or MST tests will be effective in the formation of interest.

Optionally, the methods of the present disclosure may comprise a third stage in which the effect of treatment product concentration may be evaluated for the selected formation stabilization product from the second stage, and a suitable concentration of that product is selected based on performance and fluid compatibility. Fluid compatibility studies may be performed to ensure that each component in the fluid retains its intended property or function in the presence of the recommended treatment. Fluid compatibility testing can be performed through visual observation and/or viscosity testing. One or more of the SST, MST, and/or CF tests may be used to select a suitable concentration of the treatment product. In some embodiments, the MST test may be run at different concentrations and the performance at those different concentrations may be ranked to select a single concentration. The SST and CF tests may be run using the treatment product at that concentration to confirm its performance and fluid compatibility. The final outcome is a single selected treatment and concentration the treatment product(s) that is recommended for use in an individual well.

Optionally, in some embodiments, water analysis on the fluid from the SST, MST, and/or CF test in the first stage of the methods of the present disclosure can be evaluated for one or more characteristics, including but not limited to turbidity (e.g., evidencing fines generation), conductivity (e.g., evidencing treatment elution) and carbonate concentration (e.g., evidencing mineral dissolution). The rate of mineral dissolution may be determined based on the concentration of select ions in solution. This water analysis may provide more detailed information regarding chemical reactions and reaction rates for the formation in fluids of interest. The addition of water analysis on the effluent may aid in identification of fine generation, selection of a suitable concentration of a treatment product, and identify mineral specific dissolution.

Optionally, x-ray diffraction (XRD) may be performed on the formation materials (prior to exposure to any treatment product) to determine mineralogy for the samples. XRD uses patterns of reflected beams generated when an X-ray beam was projected onto finely ground solid formation material. The compositions of the formation material may be determined by comparing the patterns generated to patterns for known minerals.

In some embodiments, the data from the SST, MST, and/or CF tests and the treatments selected using that data may be associated with the information obtained from the optional water analysis and/or formation x-ray diffraction, among other reasons, to associate the type of treatment selected with the formation's composition, mineral dissolution characteristics, and/or other properties determined from those steps. This information may be archived or stored (e.g., in a database), among other purposes, for selecting future treatments for other subterranean formations that have similar characteristics. For example, if a particular treatment was shown to be very effective in mitigating damage in a formation of a particular composition, a user might use that information to select the same treatment for another formation having a similar characteristics. Alternatively, if that treatment was shown to have little or no effect on damage in a formation of another composition, a user can use that information to eliminate possible treatments from those to be evaluated.

Among the many potential advantages to the methods and compositions of the present disclosure, only some of which are alluded to herein, the methods and systems of the present disclosure may allow field lab personnel to use performance based assessments of easy to obtain formation materials with a range of possible treatments to rank their performance and allow for customization of treatment fluids, including (but not limited to) hydraulic fracturing fluids and drilling fluids, based on the chemistry of the particular well. The methods allow lab personnel to demonstrate the water-sensitivity of formations and rank possible treatment options. In some embodiments, the methods and systems of the present disclosure may provide a quick, low-cost, field-lab deployable workflow that facilitates the selection of an optimal formation stabilization treatment to increase oil and gas production. Through the tests, users are able to evaluate formation materials to determine water-sensitivity, looking at possible damage mechanisms including (but not limited to) swelling, fines migration, precipitate migration, formation dissolution, and formation softening. In some embodiments, the methods and systems of the present disclosure may help a user recommend an optimal well-specific treatment including the appropriate product and concentration. In some embodiments, the methods and systems of the present disclosure may be able to differentiate the mineral stabilizing characteristics of chemical solutions of the same class (e.g., polymeric, oligomeric, and monomeric quaternary amines), or may be able to differentiate different types of mechanical damage in a formation (e.g., fines generation, sloughing, cracking, and/or other forms of mechanical damage).

The methods of the present disclosure may improve formation characterization for mechanism of fluid sensitivity. For example, in certain of the testing examples provided in this disclosure, the damage mechanisms in fresh or deionized (DI) water for three types of formations (bentonite clay, illite clay and Eagleford shale) was determined based on the SST (swelling) and MST (mechanical) showed more significant swelling damage for bentonite and more significant mechanical damage detected for bentonite and Eagleford. The addition of the CF test reveals more information for all three materials; fines generation for illite, the dominance of swelling over fines induced damage for bentonite and the tendency for both fines generation and swelling for Eagleford. Since the many formations have both mechanical and fines-induced damage, the CF test may provide better diagnostics for the majority of the formations being evaluated for fluid sensitivity. In some embodiments, identification of the damage mechanisms prevalent in a particular formation may facilitate better prescription of optimal treatments.

Understanding the rock fluid responses under dynamic conditions allows for better assessment of changes in permeability arising from differential pressure drops across sand pack columns. The MST and SST are static per se in that the fluid that is exposed to the rock does not change within the confines of a single test iteration. For this reason, it is difficult to assess the adsorption and desorption properties associated with treatments under flow. However, under flow the concentration of treatment fluid is in flux and if the treatment fluid does not permanently adsorb to the surface of the formation materials then subsequent pore volumes of liquid in the absence of stabilization additives would result in damage to the sand pack column. As detailed in the previous section, a new CF test has been developed to evaluate different brine and polymer-based clay stabilization formulations. The tests are performed under constant flow conditions and the flow regulator contains a built-in pressure transducer capable of capturing subtle changes in flow pressure associated with a number of potential permeability damaging scenarios.

Figure 7:
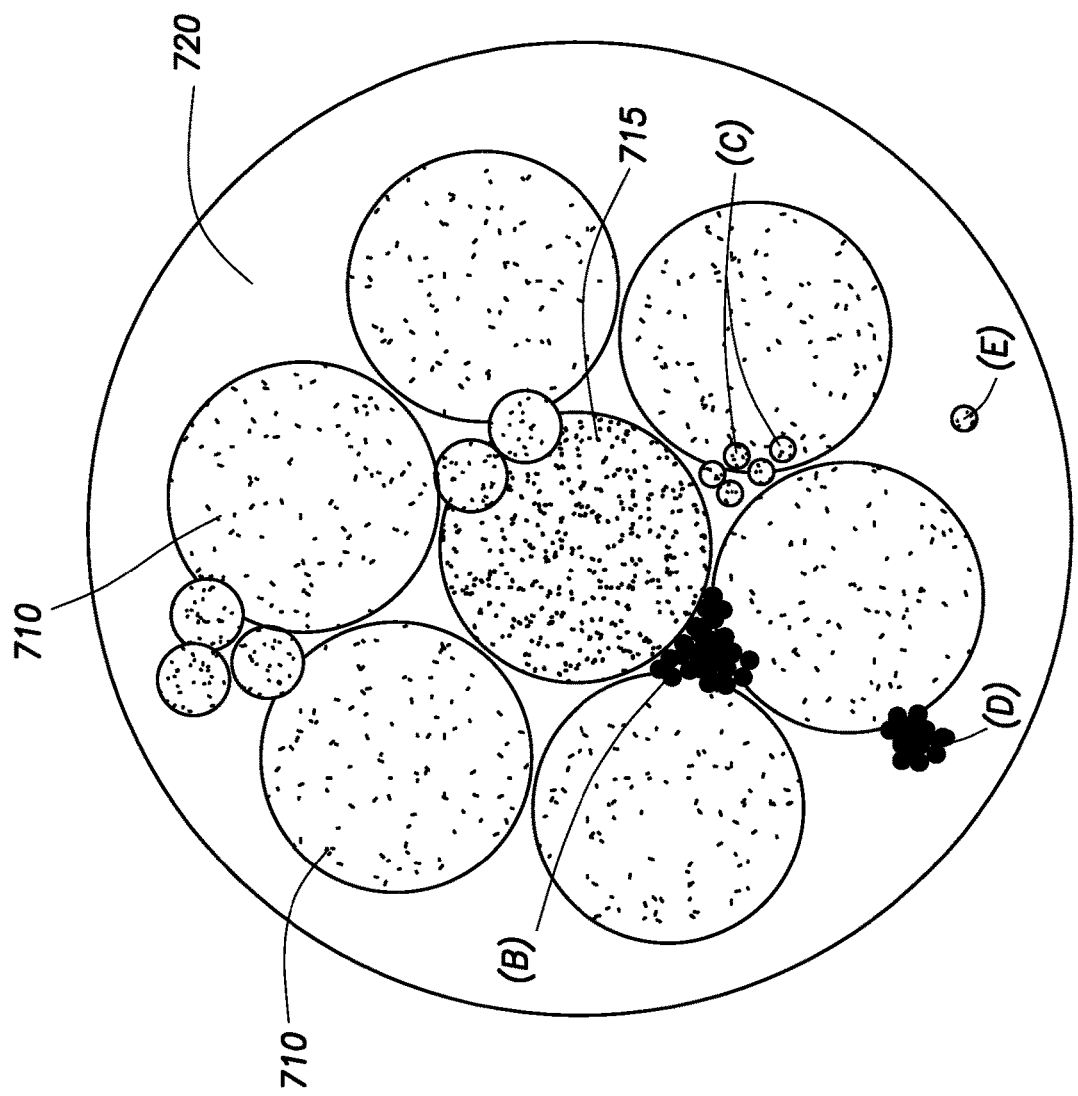
FIG. 7 is a diagram of a formation illustrating certain causes of permeability reduction under flow.

Various mechanisms may contribute to damage in a subterranean formation, certain of which are illustrated in FIG. 7. FIG. 7 shows a formation matrix that comprises several particles of sand 710 and clay 715 that are surrounded by a fluid 720. As the mixture of sand and pure clay or formation cuttings are subjected to the treatment fluid, the materials respond in a fashion that can cause swelling in which the particle loses its shape which will cause adjoining pore throats to be filled with swollen clay or shale (region (B)). If the damage is the release of fines which would also result in the fines traveling through the pore network and eventually bridging off in the pore throats causing a loss in permeability (region (C)). It is also worthy of noting that in addition to pressure responses and changes in permeability, the test involves analyzing the fluid eluted from the column with a turbidity meter. Indeed as shown in FIG. 7, fines may result from swelling (D) as well as disintegration of the particles (E) flowing out of the sand pack column.

Figure 11:
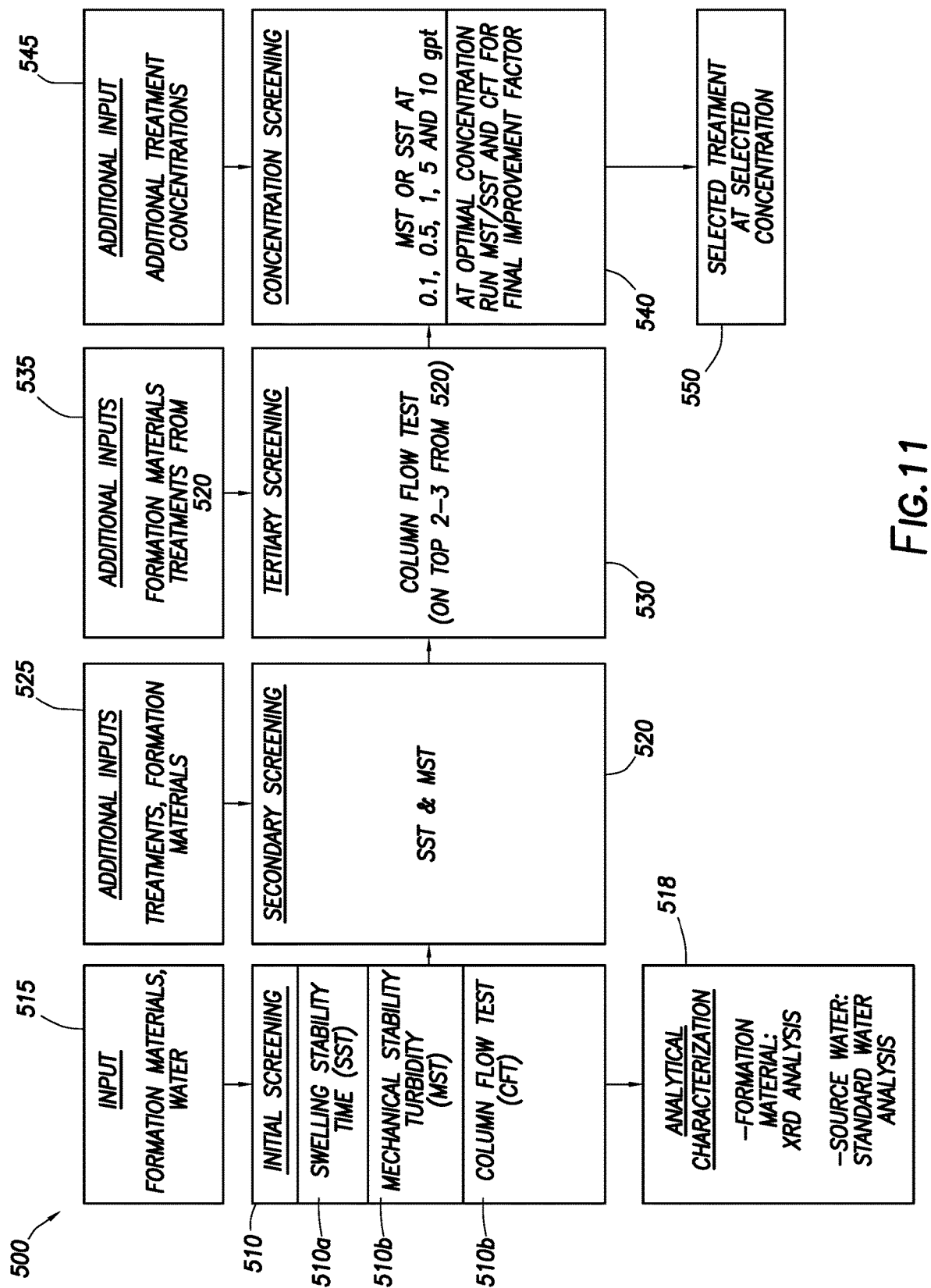
FIG. 11 is a diagram illustrating an example of an analytical workflow used to evaluate treatments to address formation damage and provide clay control.

An analytical workflow 500 as shown in FIG. 11 may be used to evaluate formation materials to determine the mechanism of fluid-sensitivity and select a suitable treatment product including the appropriate concentration. In the initial screening stage 510, the SST, MST, and CF test (510a, 510b, and 510c, respectively) may be performed using inputs 515, i.e., the formation material sample and water, to determine whether the formation exhibits fluid sensitivity. SST, MST, and CF tests may be performed in any order desired, and two or more of those tests may be performed substantially simultaneously. Optionally, at step 518, XRD analysis and/or water analysis may be performed on the fluids and/or formation materials used in this stage to provide additional information about the formation's composition, reactivity, etc.

If the formation exhibits fluid sensitivity during one or more of the SST, MST, and CF tests (e.g., the tests return a capillary suction time, turbidity, or differential pressure above a selected threshold level), the effectiveness of one or more treatments may be evaluated in a secondary screening stage 520. In this stage, additional SST and/or MST tests (whichever of those tests revealed fluid sensitivity in stage 510) are run using inputs 525, i.e., formation material samples and treatment fluids that include one or more treatment products, to determine whether the treatment mitigates the formation sample's fluid sensitivity and by how much it does so (e.g., as a percent improvement as compared to the values obtained in stage 510). One or more treatments may be identified as being most effective in mitigating fluid sensitivity in stage 520, which may be further evaluated in a tertiary screening stage 530. In this stage, additional CF tests may be run using inputs 535, i.e., formation material samples and treatment fluids that comprise the one or more treatment products identified as being most effective during stage 520. The results of the CF tests run with the treatments identified in stage 520 may be used to identify a single treatment product that is most effective from among several treatments identified as effective in stage 520 and/or to confirm that a single treatment product identified as effective in stage 520 is also effective at mitigating any fluid sensitivity demonstrated in the CF test. The CF test may rank and/or otherwise evaluated based on their effectiveness during flow, effectiveness in reducing fines migration, and/or permanency.

In the embodiment shown, secondary screening stage 520 includes the SST and MST tests, and the CF test is run in a tertiary stage 530 on a subset of the treatments evaluated in the secondary stage 520. Alternatively, in other embodiments, the CF test may be run during the secondary stage 520 on all of the same treatments evaluated using the SST and/or MST tests, and a single treatment may be identified as most effective during stage 520, in which case workflow 500 may lack a tertiary screening stage 530.

Once a single treatment is identified, the workflow optionally may include a concentration screening stage 540 in which the SST or MST test is run using inputs 545, i.e., formation material samples and treatment fluids that include the treatment product identified in stage 530 at several different concentrations (e.g., 0.1, 0.5, 1, 5, and 10 gallons per thousand gallons of fluid (gpt)). In this stage, the data from the SST or MST test may be used to select the concentration of the treatment product that most improves formation sample's fluid sensitivity (e.g., as a percent improvement as compared to the values obtained in stage 510). Once a concentration is selected, an additional CF test and/or the other of the SST and MST tests optionally may be run with the treatment product at that concentration to confirm that fluid sensitivity is not worsened in those tests. The output of stage 540 is a selected treatment 550 that includes one or more treatment products at specified concentration(s).

Among the damaging minerals that may be present originally in the formation, or may have been introduced therein, are clay materials of the smectite (montmorillonite) group such as montmorillonite, saponite, nontronite, hectorite, beidellite, and sauconite; the kaolin group such as kaolinite, nacrite, dickite, endellite and halloysite; the illite (hydrous-mica) group such as hydrobiotite, glauconite, and illite; the chlorite group (both 7 and 14 angstrom basal spacings) such as chlorite, greenalite and chamosite; clay minerals not belonging to the above groups such as vermiculite, palygorskite (attapulgite) and sepiolite; and mixed-layer (both regular and irregular) varieties of the above minerals. The clay content of the formations can include a single species of a clay mineral or several species, including the mixed-layer types of clay. The clay-containing formations need not be composed entirely of clay, but may contain other mineral components associated therewith. The clays in the formation may be of varying shapes, such as minute, plate-like, tube-like and/or fiber-like particles having an extremely large surface area.

Other types of formation damaging minerals (other than clays) may include any minerals present that will become destabilized due to interaction with the fluids or high pump rates. For example, carbonate minerals in a formation can dissolve. According to several exemplary embodiments, the subterranean formations include fine-grained, elastic sedimentary rocks composed of different mixtures of clay minerals and other minerals such as quartz, calcite, pyrite, chlorite, feldspar, opal, cristobalite, biotite, clinoptilite, gypsum, and the like. The types of minerals and their morphology in the formation may be of varying shapes and ratios.

The treatment or formation stabilization products evaluated and/or selected using the methods and systems of the present disclosure may comprise any chemical additive that may be used to prevent damage to formation materials in reaction to a water-based fluid and/or non-aqueous based fluids, such as oil, mineral oil, diesel, and condensate. Examples of formation stabilization products that may be used include, but are not limited to, potassium chloride, sodium chloride, ammonium chloride, tetramethyl ammonium chloride, cationic oligomers, cationic polymers, cationic surfactants, hydrophobic resins, transition metals, furfuryl alcohols, ethylene glycol, quaternary amines, bisquaternary amines and the like, as well as any combinations thereof.

The treatment or formation stabilization products evaluated and/or selected using the methods and systems of the present disclosure may be incorporated into a treatment fluid to be introduced into the subterranean formation to carry out a variety of subterranean treatments, including but not limited to, hydraulic fracturing treatments, acidizing treatments, cleaning treatments, and drilling operations. In hydraulic fracturing treatments, various treatment fluids such as fracturing fluids and/or pre-pad fluids may be used. Hydraulic fracturing has been utilized to stimulate the production of oil, gas and other formation fluids from subterranean formations. In hydraulic fracturing, a suitable fluid is introduced into a subterranean formation by way of a wellbore under conditions of flow rate and pressure, which are at least sufficient to create or enhance one or more fractures into a desired portion of the formation. Fracturing fluid that bleeds into the fracture face often interacts with formation materials and damages permeability of the formation adjacent to the fracture. In certain embodiments of the present disclosure, this damage can be minimized by incorporating the formation stabilization product discussed above into the fracturing fluid at an optimized concentration.

The methods and systems of the present disclosure may be used and/or performed at any stage or location relative to a treating a subterranean formation. For example, in some embodiments, the methods of the present disclosure may be performed (in whole or in part) at a well site where a well bore penetrating the subterranean formation to be treated is located. For example, one or more of the SST, MST, and/or CF tests may be performed at the well site. In those embodiments, various aspects of the systems of the present disclosure may be designed to be portable and/or readily transportable from one location to another. In other embodiments, one or more portions of the methods of the present disclosure may be performed at an offsite laboratory. In some embodiments, one or more portions of the methods of the present disclosure may be at least partially automated in that they may be performed by a computerized and/or robotic system without human intervention. In some embodiments, one or more components of the systems of the present disclosure may be designed to interface with one or more computer systems whereby data from the various tests and analytical methods described herein may be transmitted to the computer system electronically for display, storage, and/or further analysis.

EXAMPLES

In an attempt to better understand the intricacies between that the nature of the cation-counterion and the formation mineral ratios, the Codell, Mancos, Marcellus, and Bakken formation samples (examples of formations that may be evaluated or treated according to certain embodiments of the present disclosure), and were subjected to source waters obtained from four different formations varying in total dissolved salts. To elucidate the observed results a testing protocol was used to simplify the experimental condition by subjecting individual salt brines to pure clay materials and Eagle Ford shale formation cuttings. Material selection entailed subjecting a clay known for swelling: bentonite (sodium montmorillonite), as well as a clay known for producing fines in the absence of swelling, illite. The Eagle Ford shale material was selected based on the material's property to both swell and generate fines. The materials were then subjected to various testing methods believed to quantify the amount of damage or stabilization provided by each salt introduced.

Example 1

Formation Material Preparation

Formation materials were acquired from outcrops and drilling cuttings. The outcrop samples were sourced, and drilled cuttings were obtained from four North American formations—Mancos, Codell, Marcellus, and Bakken. All drilled cutting samples were sourced from the service company's stimulation or drilling operations and cleaned in the laboratory. After cleaning, the formation materials were dried in an oven to help ensure removal of all solvent, and were then ground and sieved to specific particle size distributions (PSDs).

Treatment Fluids Preparation

Source water treatment fluids were acquired for four North American wells and filtered through a 120-mesh screen to remove visible contaminates. One molar cationic treatments fluids were prepared using 6 wt. % sodium chloride (NaCl), 7 wt. % potassium chloride (KCl), 5 wt. % ammonium chloride ($NH_4C_1$), 5 wt. % calcium chloride ($CaCl_2$), or 11 wt. % tetramethylammonium chloride in fresh deionized (DI) water. The solutions were prepared and stirred until clear then ran without filtering (Table 1).

TABLE 1

Water analysis for source waters.

|  | Source Water 1 | Source Water 2 | Source Water 3 | Source Water 4 |
|---|---|---|---|---|
| Total Dissolved Solids (TDS) | 10928 | 22,545 | 83,599 | 166578 |
| pH | 8.74 | 7.54 | 3.38 | 3.2 |
| OH (mg/L) | 0 | 0 | 0 | 0 |
| $CO_3$ (mg/L) | 388.9 | 0 | 0 | 0 |
| $HCO_3$ (mg/L) | 371 | 1823.3 | 0 | 168.4 |
| Chloride (mg/L) | 6043 | 12,477 | 51,819 | 105687 |
| Sulfate (mg/L) | 90 | 3.48 | 51.6 | 100 |
| Al (ppm) | 0.33 | 0.44 | 0.9 | 1.8 |
| B (ppm) | 92.48 | 11.81 | 25.22 | 27.88 |
| Ba (ppm) | 1.13 | 2.04 | 14.36 | 3.24 |
| Ca (ppm) | 33.52 | 155 | 3289 | 11117 |
| Fe (ppm) | 0.42 | 5.31 | 1823 | 6.99 |
| K (ppm) | 104 | 28.17 | 135.5 | 434.4 |
| Mg (ppm) | 26.41 | 42.31 | 383.2 | 2280 |
| Na (ppm) | 3975 | 8044 | 28,056 | 47225 |
| Sr (ppm) | 6.5 | 27.48 | 1394 | 518.2 |
| Zn (ppm) | 815.6 | 815.6 | 798.5 |  |
| Ionic strength | 0.23348 | 0.38358 | 1.72906 | 3.29 |

X-Ray Diffraction (XRD) Analysis

XRD was used to determine mineralogy for all of the samples. The relative abundances of each mineral were calculated based on the intensity of the peaks within the pattern.

TABLE 2

XRD analysis for formation materials.

| wt (%) | Bakken | Codell | Marcellus | Mancos | Bentonite | Illite | Eagle Ford |
|---|---|---|---|---|---|---|---|
| Quartz | 43 | 32 | 36 | 46 | 4 | 23 | 42 |
| Potassium feldspar |  |  |  |  | 2 |  |  |
| Plagioclase feldspar | 5 | 8 |  |  | 6 |  |  |
| Albite |  |  |  |  |  |  | 12 |
| Calcite | 3 | 9 | 12 | 6 | trace |  |  |
| Dolomite | 5 | 4 | 1 | 12 |  |  |  |
| Pyrite | 11 | 6 | 18 | 9 |  |  |  |
| Barite | 2 | 2 |  |  |  |  |  |
| Smectite |  |  | (9) | (11) | 84 |  |  |
| Illite | 16 | 19 |  |  | 3 | 76 | 18 |
| Illite/smectite mixed layer | 15 | 20 |  |  |  |  | 20 |
| Kaolin/chlorite |  |  |  |  |  | 1 | 7 |
| Total clay | 31 | 39 | 31 | 24 | 87 | 77 | 45 |
| Cation exchange capacity (CEC) (meq/100 g) | 6 | 8 | 7 | 9 | 91 | 5 | 10 |

Testing Procedures

The SST tests in these examples were run by placing two electrodes in contact with the filter paper at 0.5 and 1.0 cm from the edge of the cylinder quantify the time necessary for the free water to wick from the inner radius to the outer radius. The capillary suction time was recorded in seconds, and the final reported value was the capillary suction time of a blank fluid (run without solids) subtracted from the capillary suction time of the slurry. Each slurry was measured in triplicate and the values are averaged.

The MST and CF tests were performed according to the standard processes described above.

Fluid Sensitivity in Source Water

Figure 3:
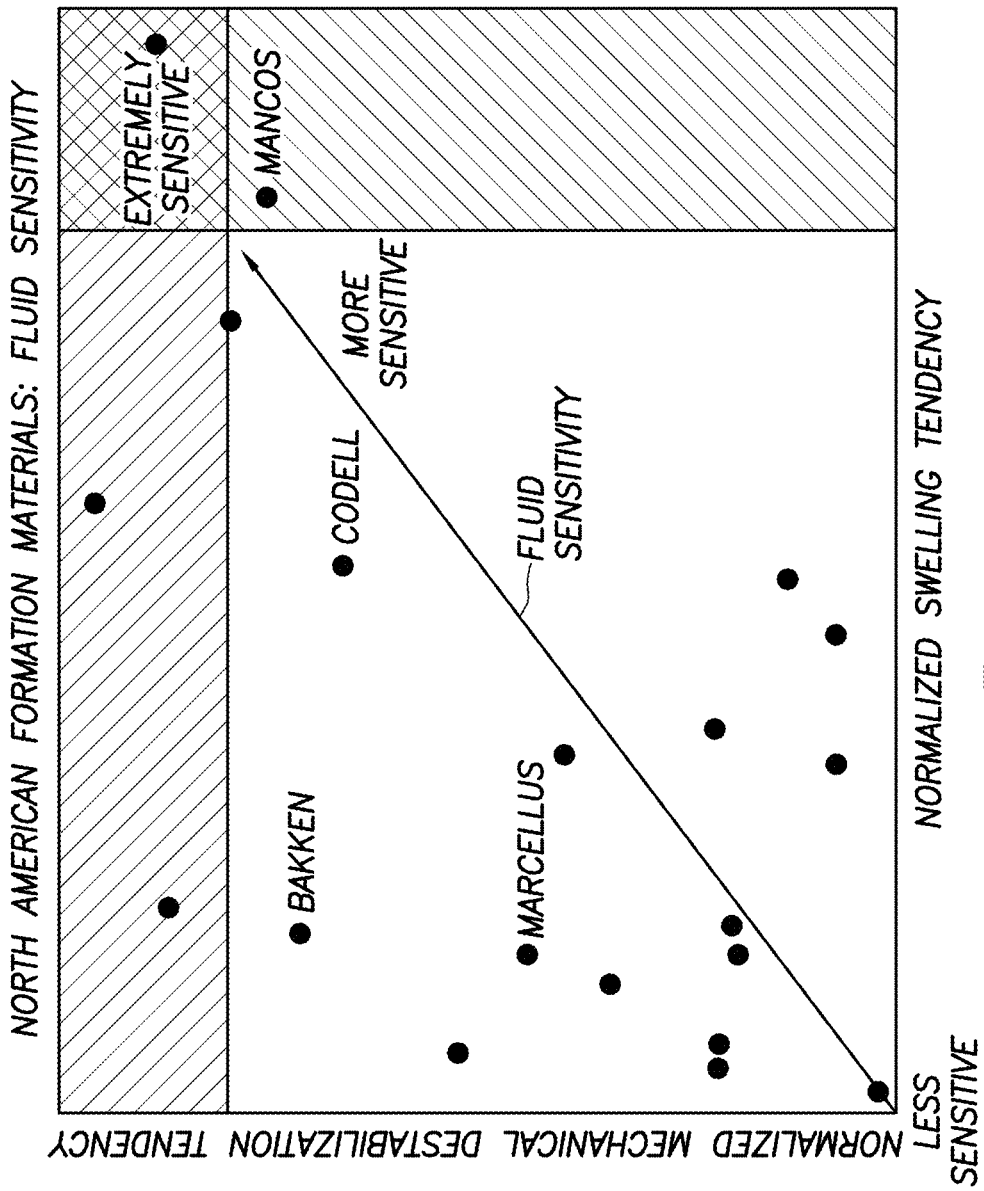
FIG. 3 is a plot illustrating fluid sensitivity for Mancos, Codell, Bakken, and Marcellus formation cuttings in fresh water compared to other North American shale formation materials.

Stimulation treatment designs containing source water or reclaimed produced water are believed to help control formation damage through reduced cation exchange and lower osmotic potential. To better understand the role that source waters have on the formation damage, formation samples from the Mancos, Codell, Marcellus, and Bakken formation were evaluated in fresh DI water and four source waters using both SST and MST testing as described above. First, the formations were characterized based on their damage potential for swelling or mechanical destabilization in fresh DI water. FIG. 3 is a plot of the SST (swelling tendency) vs. MST (mechanical destabilization) normalized results for fluid sensitivity for all four formation materials compared to other North American shale formation materials characterized by the same tests. In the data shown in FIG. 3, the formation materials are normalized to the mean of all samples and categorized as extremely fluid sensitive if their response exceeds twice the average of all formations. Of the four evaluated for this test, Mancos is the only formation that exhibits extreme fluid sensitivity; it is extreme for swelling and very high in mechanical destabilization. Codell has higher swelling tendency than Bakken while Bakken has more mechanical damage. Marcellus has low swelling and moderate mechanical damage. Next the effects of source water were determined based on the change in damage potential relative to the fresh water.

Figure 4:
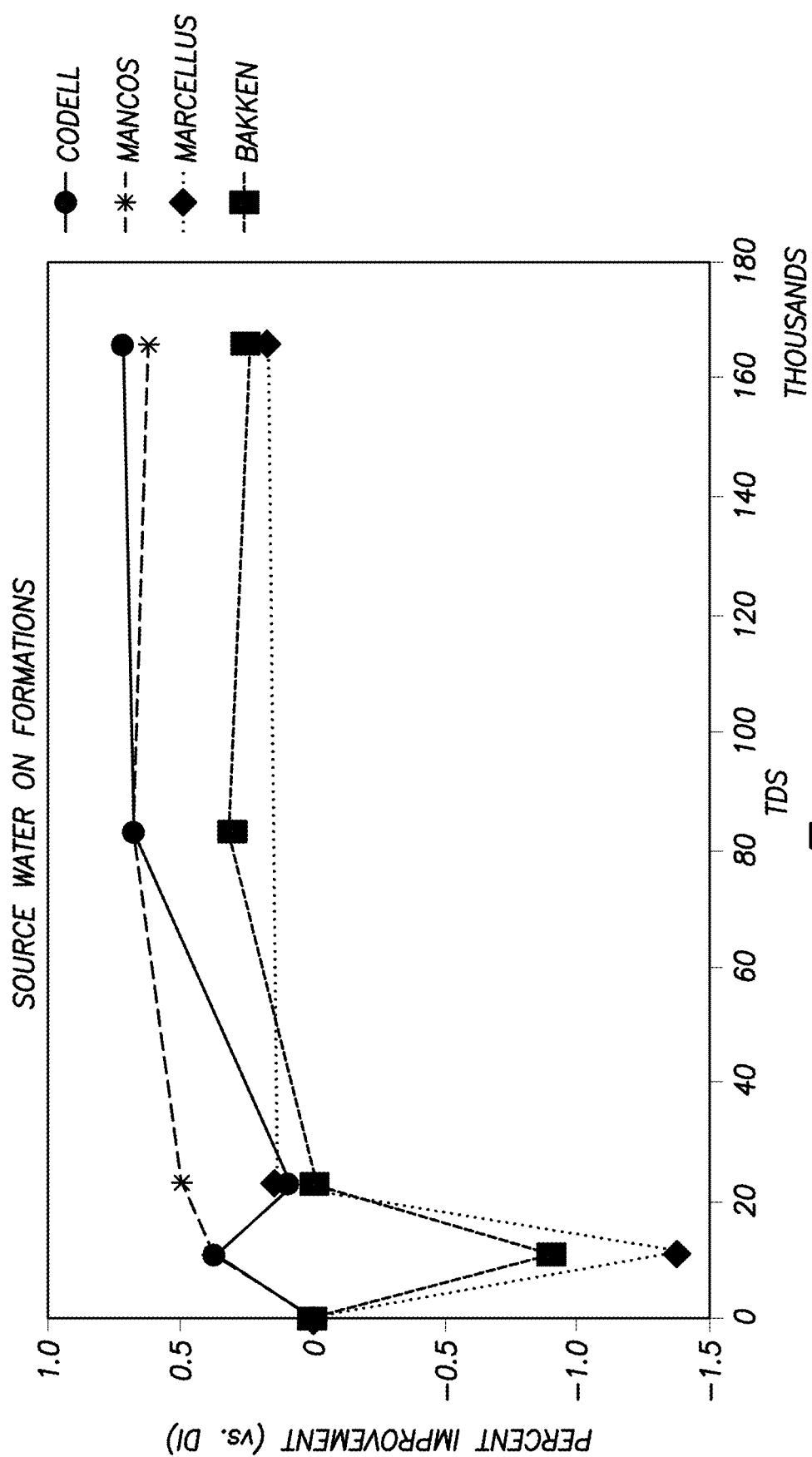
FIG. 4 is a graph illustrating data regarding source water effects on formation materials.

Percent improvement was determined as the percent difference from the source water to the DI water for each formation material in SST and MST averaged together. The source water was characterized using a standard water analysis for specific anion and cation concentrations, pH, total dissolved solids (TDS), and ionic strength. FIG. 4 is a graph of the percent improvement is plotted versus TDS for each of the formation materials. As shown in FIG. 4, the source water did not have the same effect for all four formations. The overall effects are most similar for Bakken and Marcellus (low swelling formations) and Codell and Mancos (high swelling formations). When evaluating the effects from increasing the TDS, Mancos shows the expected trend; the percent improvement increases with TDS until it reaches a plateau. Improvement factors for Marcellus and Bakken were not as high in source water; however, at low TDS there is an increase in the formation damage resulting in a negative improvement for that fluid system on these two low swelling formations.

The data was screened for statistically significant factors, and the bicarbonate, CEC, ratio of sodium to potassium (Na/K) and their interactions had the lowest p-values meaning they were most significant factors for the percent improvement. The low TDS fluid had the highest bicarbonate concentrations and could have reacted with the carbonate in theses formations to reduce the percent improvement. Codell was resistant to the bicarbonate effect, however its response to the 20,000 TDS decreased compared to the lower TDS fluid and compared to Mancos. The 20,000 TDS fluid has the highest concentration of sodium ions relative to the potassium ions; therefore, the cations and their ratio seem to be a significant contributing factor to formation damage on formation materials.

Example 2

In an attempt to further elucidate the role of the cation on the formation damage effect, a series of experiments were performed using materials with more specific damage mechanisms. Formation materials chosen for the next set of experiments were: Bentonite, smectite clay (as a swelling material), pure illite clay (as a material to produce fines in the absence of swelling), and Eagle Ford shale cuttings (as a natural complex sample that contain smectite, illite, and some carbonate).

Figure 5A:
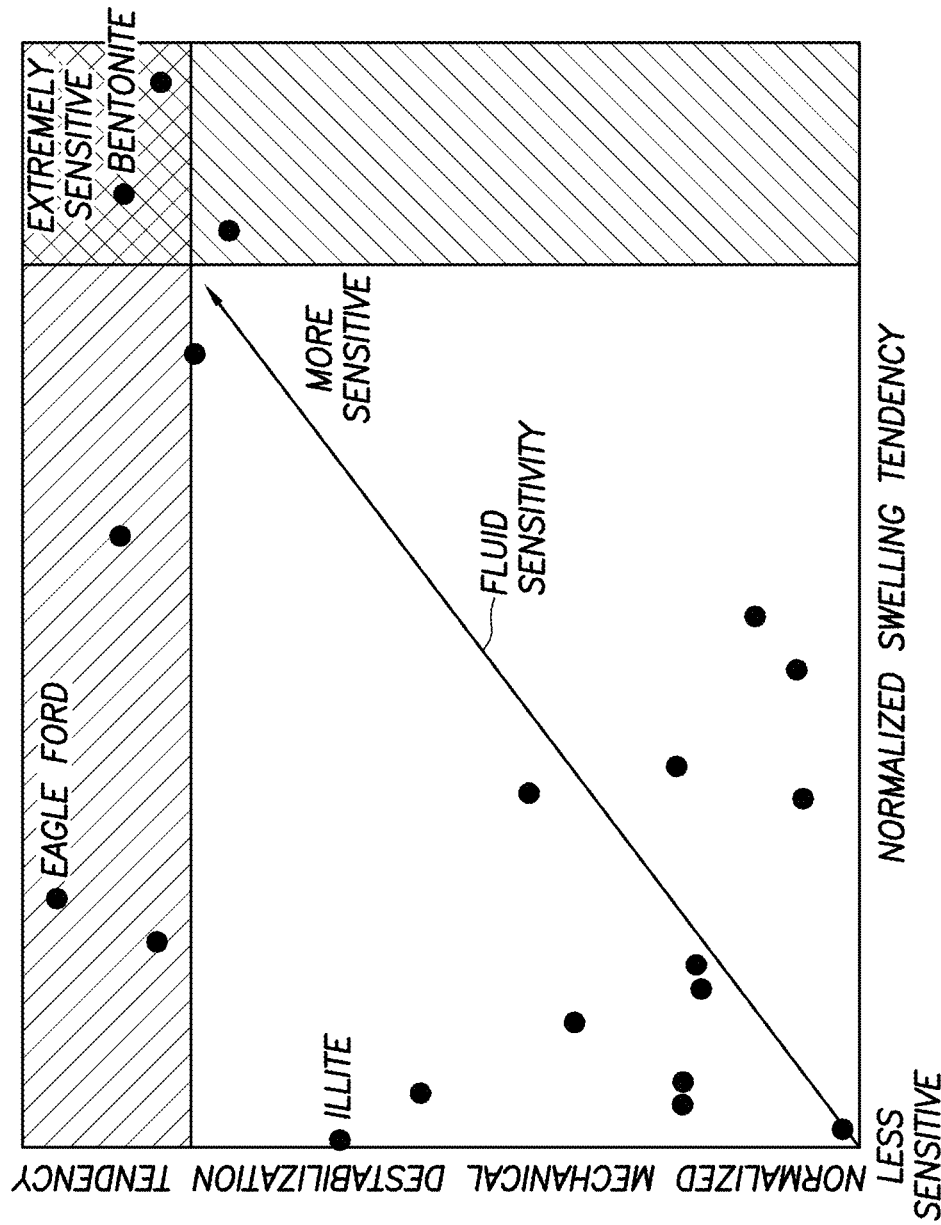
FIGS. 5A and 5B are plots illustrating fluid sensitivity for bentonite, illite, and Eagle Ford formation cuttings in fresh water compared to other North American shale formation materials.
Figure 5B:
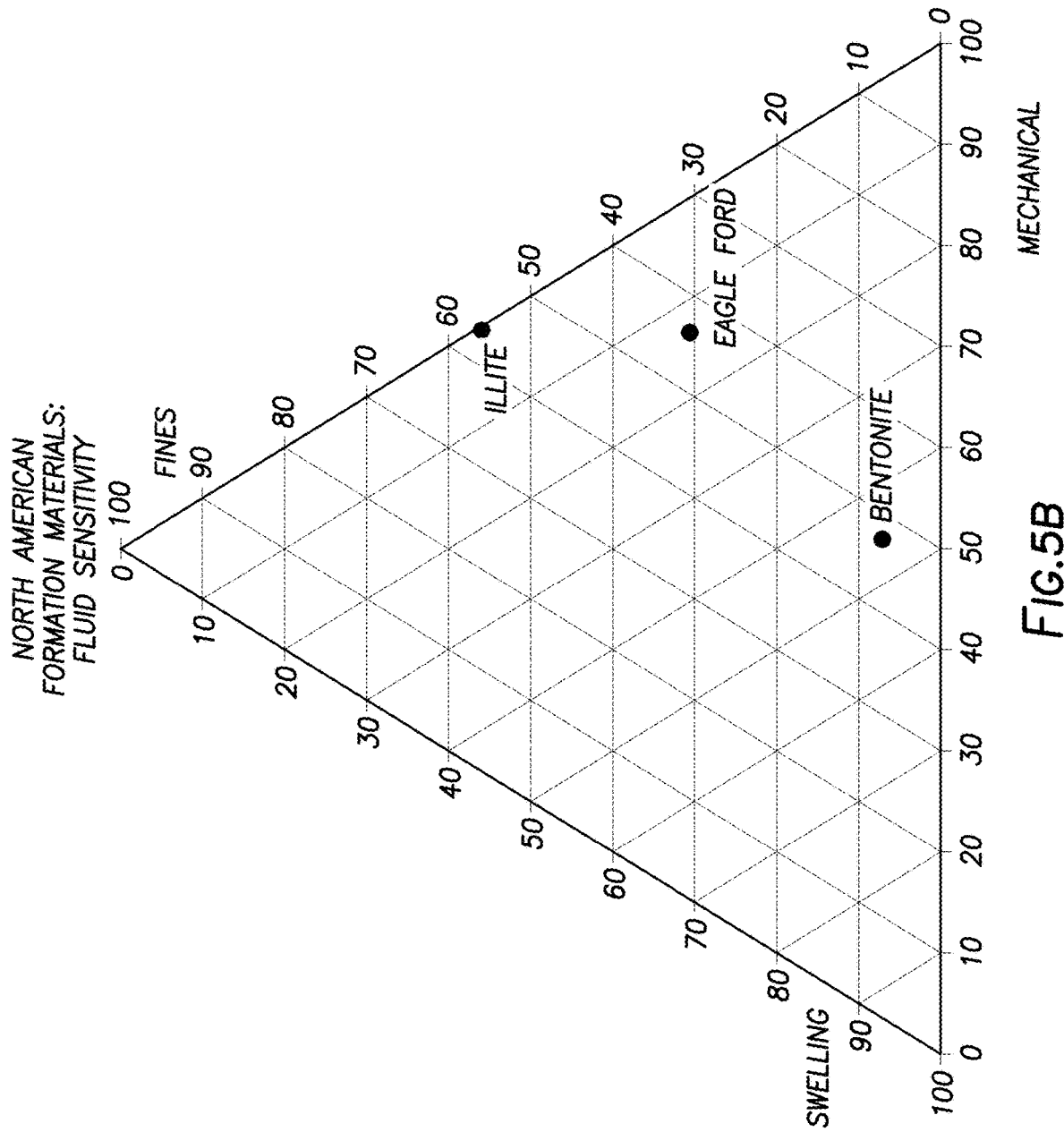

The damage effects were confirmed upon further inspection with SST and MST in DI water according to the same procedures used in Example 1. FIG. 5A is a plot of the SST (swelling tendency) vs. MST (mechanical destabilization) normalized results for fluid sensitivity for all three formation materials. In FIG. 5, it can be seen that the bentonite has a tendency to swell, which induces the generation of fines, while the illite has no tendency to swell and nearly all of the damage from the hydration of illite causes to fines generation. The Eagle Ford provides a midpoint wherein the material has a tendency to both swell and generate fines, albeit with a more significant contribution from the later. Evaluation of the damage mechanism for bentonite exposure of the dry bentonite clay to distilled water results in a colloidal dispersion of very fine particles. The driving force behind the complete loss of granular texture and consistency is the hydration of intercalated cations, predominately sodium, by the "fresh" distilled water. During the process of balancing the osmotic potential as the clay hydrates, the cations are surrounded by water molecules causing particles to expand rapidly and rearrange into an expanded structure. Fresh water on illite clay also hydrates or displaces the interlayer cations, which are predominately potassium; this hydration results in the loss of cohesion forces between the clay layers and causes detachment in the form of fine particles. The Eagle Ford shale cuttings exhibited more fines generation than swelling; however, there was a contribution of swelling to the fluid sensitivity. However, the results shown in FIG. 5A show that the original service utilizing two tests does not emphasize the damage potential of the illite clay sample. With the original service illite does not appear to have a lot of damage and it is not clear what mechanism is leading to the extreme MST damage detected for Bentonite and Eagleford. FIG. 5B is a plot of the SST (swelling tendency) vs. MST (mechanical destabilization) vs. CF (column flow for fines generation) normalized results for fluid sensitivity for all three formation materials. The addition of the CF data reveals more information for all three materials; major fines generation for illite, the dominance of swelling over fines induced damage for Bentonite and the higher tendency for fines generation for Eagle Ford. Since the many North American formations have mechanical and fines induced damage, the improved test provides better diagnostics for the majority of the formations.

Example 3

This example tests a hypothesis that brine solution at 1-M concentrations: 6 wt. % sodium chloride (NaCl), 7 wt. % potassium chloride (KCl), 5 wt. % ammonium chloride (NH$_4$Cl), 11 wt. % tetramethylammonium chloride (TMAC), and 5 wt. % calcium chloride (CaCl$_2$) can provide equivalent temporary clay stabilization, thereby preventing formation damage. However, not all of the dissolved cations in the brine solutions offer the same level of clay protection when exposing the brines to pure bentonite and illite clay materials. In addition, treatment of the Eagle Ford shale cuttings has shown that some dissolved cations in solution performed worse than water.

FIGS. 6A-6C are a series of plots showing a comparison of the MST to SST testing results for the bentonite (A), illite (B), and Eagle Ford (C) formation materials evaluated in Example 2 in different brine solutions. As can be understood from FIGS. 6A-6C, with respect to bentonite, the brine solutions look to prevent the characteristic swelling response observed when fresh, or soft, water is exposed to bentonite. With the exception of NaCl, the other suite of cations seems to provide sufficient protection to prevent the bentonite from swelling. In a similar fashion, but to a lesser extent, both KCl and NH$_4$Cl prevented the illite from damage when subjected to mechanical agitation. Illite does not swell, so SST experimental values are not significant. This data also illustrates that both choline chloride (C$_5$H$_{14}$ClNO) and NaCl do not offer the same level of protection toward mechanical agitation (see MST results under (B)) as the KCl and NH$_4$Cl.

Subjecting the Eagle Ford shale cuttings to both the MST and SST resulted in fairly evenly distributed product performance. Initial inspection of the Eagle Ford performance data suggests KCl does well to prevent the shale from both fines generation and swelling. The results do not seem to follow the Hofmeister series for the hydration of cations as the KCl slightly outperforms the NH$_4$Cl and NaCl brine performs much worse than the CaCl$_2$ brine. Moreover, the results suggest that the NaCl performs worse than water at preventing mechanical damage with the Eagle Ford cuttings (C).

Example 4

Figure 8A:
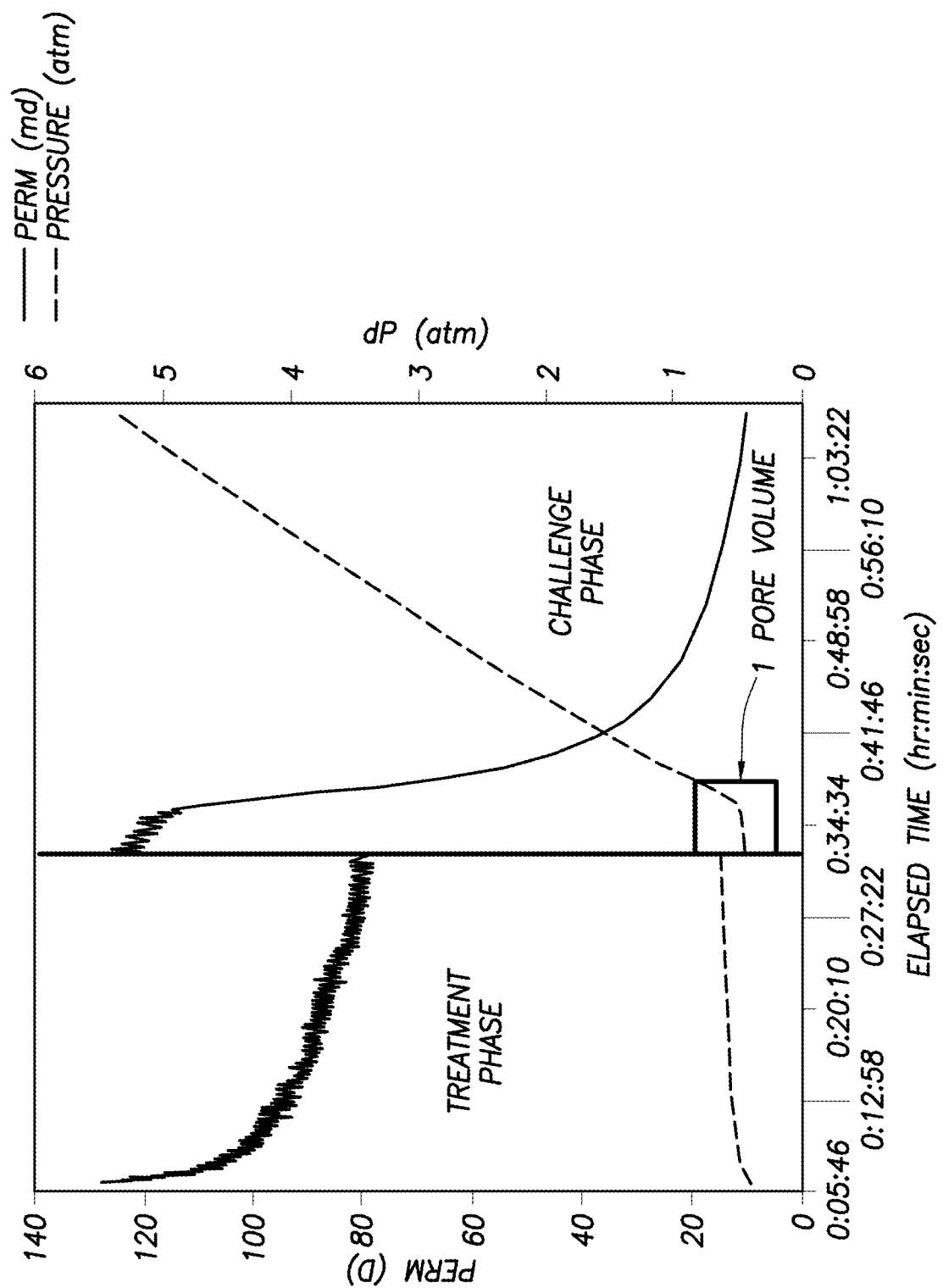
FIGS. 8A and 8B are plots illustrating idealized data relating to the performance of different treatments in column flow tests over time according to certain embodiments of the present disclosure.
Figure 8B:
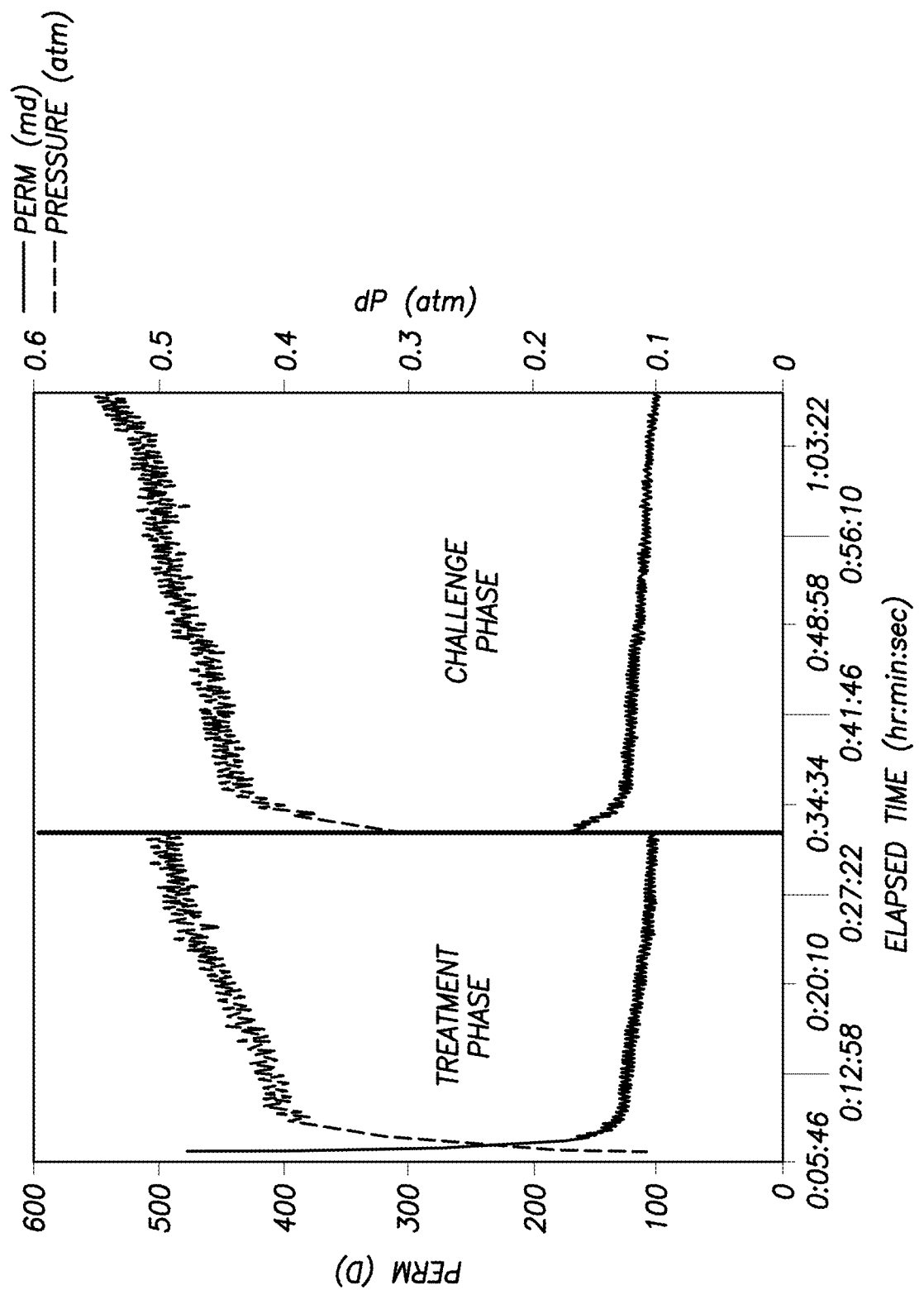

As discussed above, one advantage of the methods and systems of the present disclosure is the ability to assess the permanency of the treatment fluid applied to a formation. FIGS. 8A and 8B illustrate idealized data from column flow tests (divided into the "treatment phase" and the "challenge phase" described above) performed using two different treatment products. The scenario depicted in FIG. 8A reflects typical results for a brine-based formulation in which the viscosity of the solution is very low and does not exhibit a large amount of pressure during the treatment phase (lower blue line). However, as the mobile phase is changed from the treatment fluid to distilled water after the first pore volume, it is expected that all of the brine would have been displaced. Indeed, this very response can be seen in the "challenge phase" portion of FIG. 8A: as the brine is pushed out of the column the pressure begins to rise rather rapidly. This observation is likely caused by fresh water induced swelling or fines migration that leads to clogged pore throats resulting in loss of permeability.

In contrast, the scenario depicted in FIG. 8B reflects typical results for permanent treatment applications usually associated with polymer-based clay stabilizing formulations. As can be seen in the "challenge phase" region, pressure looks to slowly increase overtime as the permeability exhibits a slight decline which is a stark difference from what is observed in the "challenge phase" region of FIG. 8A.

Example 5

In the context of types (salt vs. organic-monomeric vs. polymeric) and classes (temporary vs. permanent) of clay stabilization products, aside from a few reported inorganic polymers, brine solutions are typically not used for permanency. Given the mechanism of action (i.e., reducing the osmotic potential via lowering the rate of cationic exchange), it is not likely that protection of the clay or shale minerals will continue once the cations are no longer present in the fluid. FIG. 9 plots the normalized permeability of those same sandpacks over time during the "challenge phase" of the column flow test. After the sandpack has been subjected to 3 PVs of the treatment fluid, the sandpack is then "challenged" with distilled or fresh (cation free) water to assess the permanency of the applied treatment. It is rational to conclude that this procedure is best suited for both inorganic as well as organic polymers, treatments that are expect to adsorb or react with the formation to provide some level of protection via film formation, wettability modification, or lowering of the cation exchange rate (hydrophobic modification).

The stark difference in performance between salt brines and monomeric organic salt brines (TMAC) is showcased in FIG. 9. In addition to the aforementioned differences, also depicted in FIG. 9 is the change in performance from the monomeric-TMAC to the oligomeric- and polymeric-quaternary amine. The last point highlights the utility of the methods and systems of the present disclosure, as the column flow test has the sensitivity to differentiate between similar product types.

Example 6

Figure 10B:
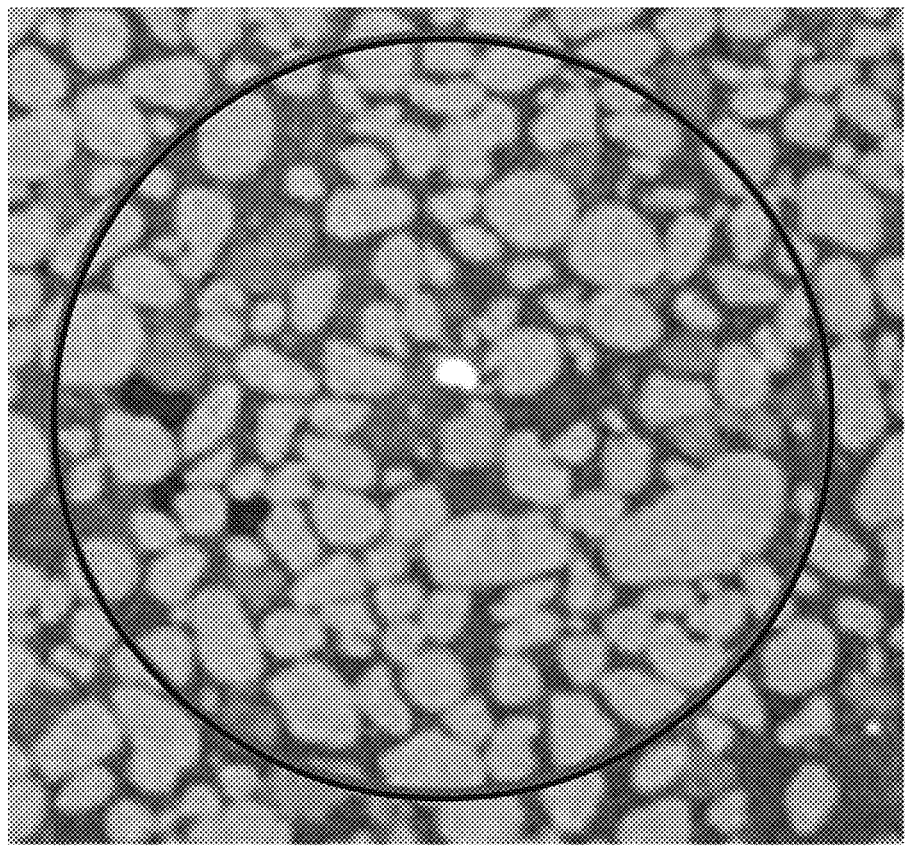
FIGS. 10A and 10B are X-ray computerized tomography (CT) images of a sandpack in a column flow test according to certain embodiments of the present disclosure before and after testing, respectively.
Figure 10A:
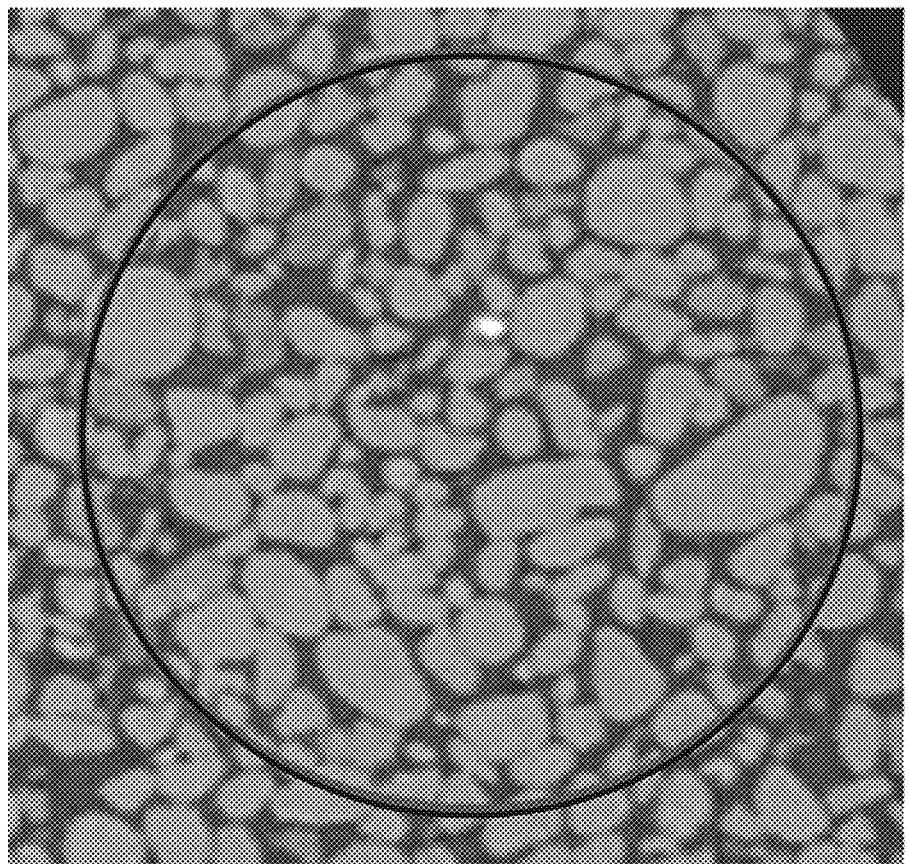

To provide an additional evaluation of the damage within the sand pack column, during CF, X-ray computerized tomography (CT) scans were run on the sand pack before and after a fresh water "challenge phase. FIG. 10A is an image of the sandpack before the "challenge phase", and FIG. 10B is an image of the same sandpack after the "challenge phase". As shown, the premium sand are the bright spots and the bentonite materials are slightly darker in intensity due to the difference in density for the quartz (2.7 g/cm$^3$) verse bentonite (2.2 g/cm$^3$), the darkest areas represent the water (1.0 g/cm$^3$) or air (0.001 g/cm$^3$) within the column. The very brightest point in the image is a pyrite mineral; with a density of 4.8 g/cm$^3$, these minerals become very obvious in CT images. Evaluation of the same area before and after fluid flush showed no significant movement or compaction of the sand grains, meaning that the decrease in permeability is not due to the compaction of the sand grains under flow. There is a minor amount of shifting in the sand grains adjacent to the clay particles because of the spreading of the swollen bentonite. Also noticeable in the column after contact with the fresh water is the addition of another intermediate intensity gray color; this is the hydrated bentonite material. Almost all of the pores in the picture on the right are the intermediate gray color showing that the bentonite essentially blocks all the pore throats. The upper section of the after image has four very dark spots, which were determined to be trapped air or water, because the dark spots were not continuous (or connected) throughout the column. This analysis confirms that the permeability decrease measured in the CF tests is attributed to the clay damage to the sand pack permeability.

Example 7

Figure 12A:
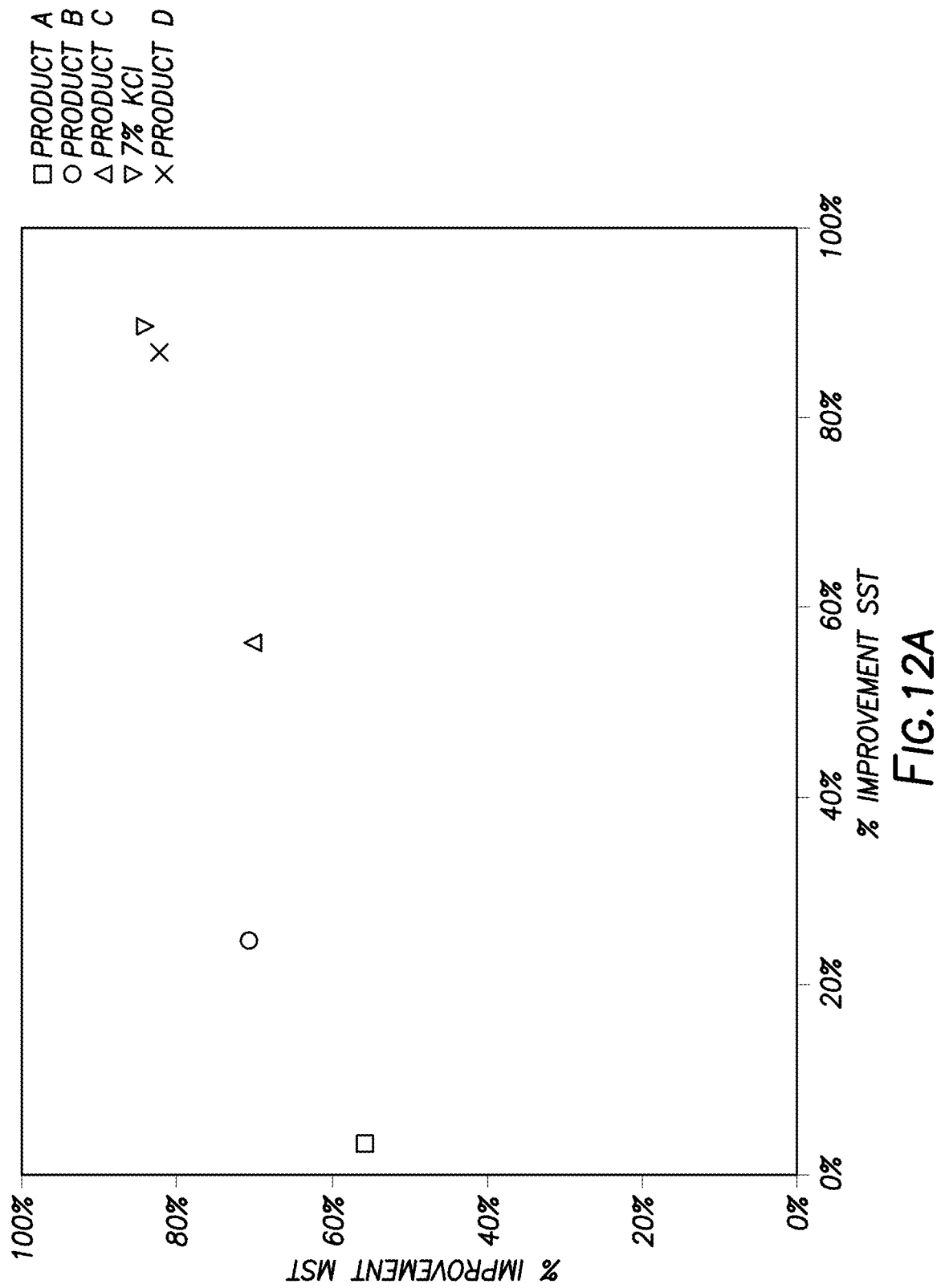
FIG. 12A is a plot illustrating data relating to the performance of different clay stabilization treatments in SST and MST tests according to certain embodiments of the present disclosure.

FIG. 12A shows the results of SST and MST tests for various clay stabilization treatments (percent improvement over DI water) for a given formation. A treatment using a 7%

Figure 12B:
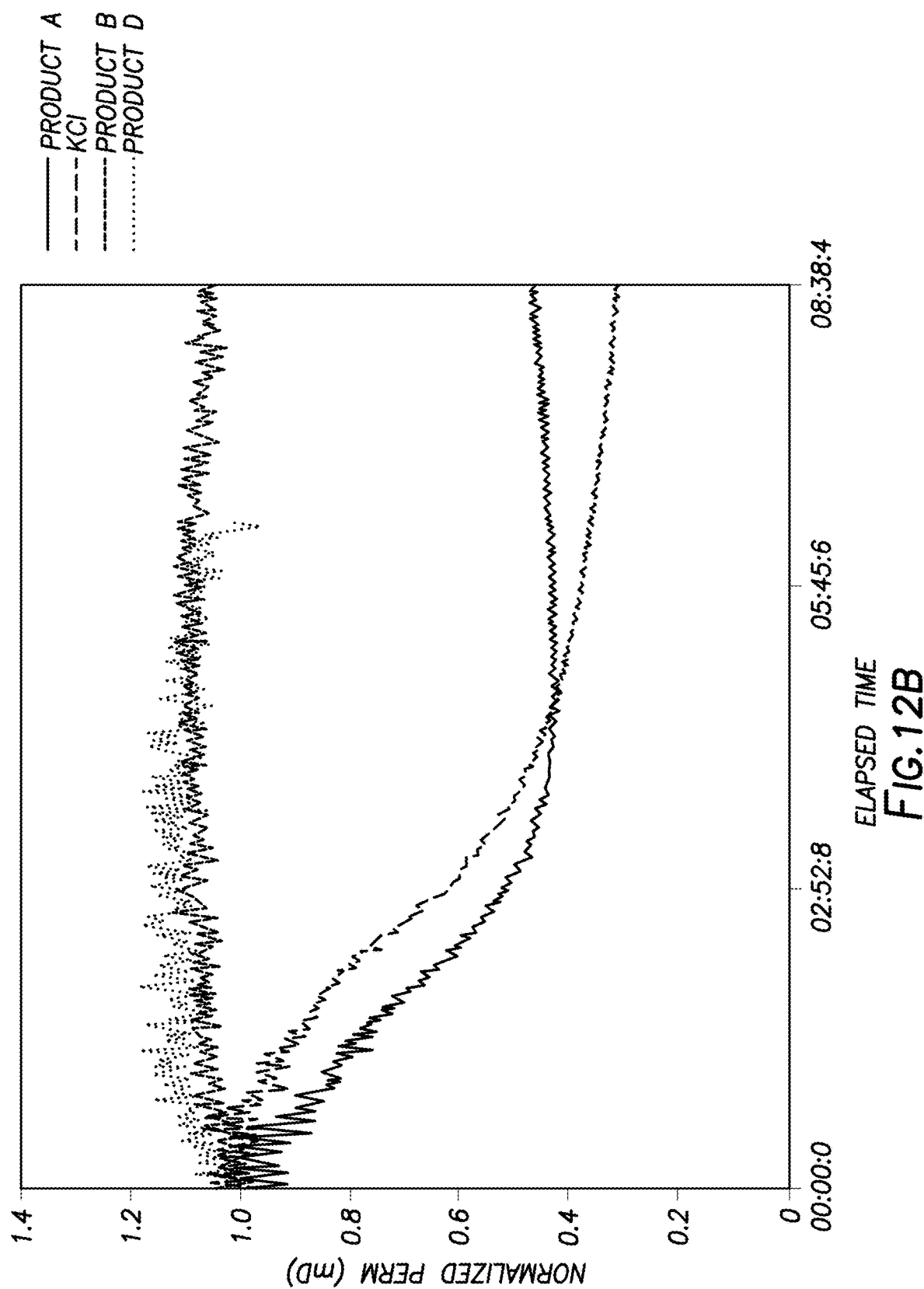
FIG. 12B is a plot illustrating data relating to the performance of the clay stabilization treatments from FIG. 12A in column flow tests according to certain embodiments of the present disclosure.

KCl aqueous solution and four different commercially-available treatment products were tested: Product A (a clay-control material), Product B (a clay stabilization additive), Product C (a clay stabilization additive), and Product D (a clay stabilization additive). FIG. 12B shows normalized permeability over time during the challenge phase of column flow tests using those same treatments. In a product evaluation workflow using only SST and MST tests (FIG. 12A), treatments using 7% KCl and Product D overlap in performance, making the optimal product recommendation difficult to determine. However, the column flow test (FIG. 12B) shows that the sandpack treated with 7% KCl has a steep decrease in permeability after a certain volume of fresh water challenge, indicated that it is a temporary treatment while the sandpack treated with Product D remains consistent in permeability throughout the DI challenge phase, indicating that it is a more permanent treatment. Thus, the methods and systems of the present disclosure may provide better product differentiation based on treatment under dynamic flow conditions and permanency.

In some embodiments, the methods of the present disclosure comprise: providing a formation material from a subterranean formation; adding a first portion of a test fluid to a first portion of the formation material to form a first mixture; adding a second portion of the test fluid to a second portion of the formation material to form a second mixture; agitating the first and second mixtures; measuring a capillary suction time of the first mixture; measuring a turbidity of the second mixture; placing a test sandpack comprising a third portion of the formation material in a column; passing a third portion of the test fluid through the test sandpack to collect an effluent; measuring a differential pressure across the test sandpack; measuring a turbidity of the effluent; and selecting a formation stabilization treatment for the subterranean formation based at least in part on one or more of the capillary suction time of the first mixture, the turbidity of the second mixture, the differential pressure across the test sandpack, and the turbidity of the effluent.

In some embodiments, the methods of the present disclosure comprise: measuring a capillary suction time or a turbidity of material from a subterranean formation in water; measuring differential pressure across a sandpack comprising material from the subterranean formation during a column flow test using water; measuring a capillary suction time or a turbidity of material from the subterranean formation in each of a plurality of different formation stabilizer solutions; calculating a percent improvement of capillary suction time or turbidity for each of the plurality different formation stabilizer solutions over water; selecting two or more formation stabilizer solutions from the plurality of different formation stabilizer solutions based on the calculated percent improvements; measuring a differential pressure across a sandpack comprising material from the subterranean formation during each of two or more column flow tests each using one of the selected formation stabilizer solutions; calculating a percent improvement of differential pressure across the sandpack for each of the selected formation stabilizer solutions over water; and selecting a single formation stabilizer solution based at least in part on the calculated percent improvements of differential pressure across the sandpack.

In some embodiments, the methods of the present disclosure comprise: measuring a capillary suction time and a turbidity of material from a subterranean formation in water; measuring a differential pressure across a sandpack comprising material from the subterranean formation during a column flow test using water; measuring a capillary suction time and a turbidity of material from the subterranean formation in each of a plurality of different formation stabilizer solutions; calculating a percent improvement of capillary suction time and turbidity for each of the plurality of different formation stabilizer solutions over water; selecting two or more formation stabilizer solutions based on the calculated percent improvements; measuring a differential pressure across a sandpack comprising material from the subterranean formation during each of two or more column flow tests each using one of the selected formation stabilizer solutions; calculating a percent improvement of differential pressure across the sandpack for each of the selected formation stabilizer solutions over water; and selecting a single formation stabilizer solution based at least in part on the calculated percent improvements of differential pressure across the sandpack.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to those skilled in the art having the benefit of the teachings herein. While numerous changes may be made by those skilled in the art, such changes are encompassed within the spirit of the subject matter defined by the appended claims. Furthermore, no limitations are intended to the details of construction or design herein shown, other than as described in the claims below. It is therefore evident that the particular illustrative embodiments disclosed above may be altered or modified and all such variations are considered within the scope and spirit of the present disclosure. In particular, every range of values (e.g., "from about a to about b," or, equivalently, "from approximately a to b," or, equivalently, "from approximately a-b") disclosed herein is to be understood as referring to the power set (the set of all subsets) of the respective range of values. The terms in the claims have their plain, ordinary meaning unless otherwise explicitly and clearly defined by the patentee.

What is claimed is:
1. A method comprising:
providing a formation material from a subterranean formation;
adding a first portion of a test fluid to a first portion of the formation material to form a first mixture;
adding a second portion of the test fluid to a second portion of the formation material to form a second mixture;
agitating the first and second mixtures;
measuring a capillary suction time of the first mixture using capillary suction test equipment located at a field lab locale or at a well site where a well bore penetrating at least a portion of the subterranean formation is located;
measuring a turbidity of the second mixture using mechanical stability test equipment located at the field lab locale or at the well site, wherein measuring the turbidity comprises detecting an amount of light from a light source that passes through a vial containing the second mixture to a detector on an opposite side of the vial after agitating the second mixture in the vial;
placing a test sandpack comprising a third portion of the formation material in a column; and
measuring a differential pressure across the test sandpack using column flow test equipment located at the field lab locale or at the well site; and selecting a formation stabilization treatment for the subterranean formation based at least in part on the capillary suction time of the first mixture, the turbidity of the second mixture, and the differential pressure across the test sandpack.

2. The method of claim 1 further comprising introducing the at least one formation stabilization treatment into at least a portion of the subterranean formation.

3. The method of claim 1 wherein the test fluid comprises water.

4. The method of claim 1 wherein the formation stabilization treatment comprises at least one treatment additive selected from the group consisting of: potassium chloride, sodium chloride, ammonium chloride, tetramethyl ammonium chloride, a cationic polymer, a cationic surfactant, a hydrophobic resin, a transition metal, furfuryl alcohol, ethylene glycol, a quaternary amine, a bisquaternary amine, and any combination thereof.

5. The method of claim 1 wherein selecting the formation stabilization treatment for the subterranean formation further comprises:
mixing two or more additional portions of the formation material with each of a plurality of treatment fluids to form a plurality of treated mixtures, wherein each of the plurality of treatment fluids comprises at least one treatment product;
measuring a capillary suction time of each of the plurality of treated mixtures;
measuring a turbidity of each of the plurality of treated mixtures;
placing a treatment sandpack comprising an additional portion of the formation material in a column;
passing one of the plurality of treatment fluids through the treatment sandpack;
measuring a differential pressure across the treatment sandpack;
selecting a formation stabilization treatment for the subterranean formation, the formation stabilization treatment being one of the plurality of treatment fluids, based at least in part on
a comparison of the capillary suction time of each of the plurality of treated mixtures with the capillary suction time of the first mixture,
a comparison of the turbidity of each of the plurality of treated mixtures with the turbidity of the second mixture, and
a comparison of the differential pressure across the treatment sandpack with the differential pressure across the test sandpack.

6. The method of claim 5 further comprising:
providing a second plurality of treatment fluids comprising a treatment product from the selected formation stabilization treatment at one or more different concentrations;
mixing additional portions of the formation material with each of the second plurality of treatment fluids to form a second plurality of treated mixtures;
measuring capillary suction time of each of the second plurality of treated mixtures; and
selecting a concentration of the treatment product for the formation stabilization treatment based at least in part on the capillary suction times of the second plurality of treated mixtures.

7. The method of claim 6 further comprising:
placing a second treatment sandpack comprising an additional portion of the formation material in a column;
passing a treatment fluid comprising the selected treatment product at the selected concentration through the second treatment sandpack; and
measuring a differential pressure across the second treatment sandpack.

8. The method of claim 5 further comprising:
providing a second plurality of treatment fluids each comprising a treatment product from the selected formation stabilization treatment at one or more different concentrations;
mixing additional portions of the formation material with each of the second plurality of treatment fluids to form a second plurality of treated mixtures;
measuring a turbidity of each of the second plurality of treated mixtures; and
selecting a concentration of the treatment product for the formation stabilization treatment based at least in part on the turbidities of the second plurality of treated mixtures.

9. The method of claim 8 further comprising:
placing a second treatment sandpack comprising an additional portion of the formation material in a column;
passing a treatment fluid comprising the selected treatment product at the selected concentration through the second treatment sandpack; and
measuring a differential pressure across the second treatment sandpack.

10. The method of claim 5, wherein selecting the formation stabilization treatment from the plurality of treatment fluids comprises:
identifying one or more damage mechanisms within the formation material based on the capillary suction time of the first mixture, the turbidity of the second mixture, and the differential pressure across the test sandpack, the one or more damage mechanisms being selected from the group consisting of: swelling, mechanical instability, and fines production;
determining an amount by which each of the plurality of treatment fluids addresses or reduces an effect of the one or more identified damage mechanisms based at least in part on:
the comparison of the capillary suction time of each of the plurality of treated mixtures with the capillary suction time of the first mixture,
the comparison of the turbidity of each of the plurality of treated mixtures with the turbidity of the second mixture, and
the comparison of the differential pressure across the treatment sandpack with the differential pressure across the test sandpack; and
selecting one of the plurality of treatment fluids that addresses or reduces the effect of the one or more identified damage mechanisms by a largest amount as the formation stabilization treatment.

11. The method of claim 1 wherein one or more of the capillary suction time of the first mixture, the turbidity of the second mixture, and the differential pressure across the test sandpack, are measured using equipment located at a well site where a well bore penetrating at least a portion of the subterranean formation is located.

12. The method of claim 1 further comprising:
analyzing a sample of the material from the subterranean formation using an x-ray diffraction process to determine one or more mineralogical properties of the subterranean formation; and storing data relating to the one or more mineralogical properties of the subterranean formation and the selected formation stabilization treatment for the subterranean formation.

13. The method of claim 1 further comprising:
passing a third portion of the test fluid through the test sandpack to collect an effluent;
analyzing the composition of a fluid from one or more of the first mixture, the second mixture, and the effluent; and
storing data relating to the composition of the fluid and the selected formation stabilization treatment for the subterranean formation.

14. The method of claim 1, wherein the capillary suction test equipment, the mechanical stability test equipment, and the column flow test equipment are all located at the field lab locale.

15. The method of claim 1, wherein the capillary suction test equipment, the mechanical stability test equipment, and the column flow test equipment are all located at the well site.

* * * * *